United States Patent
Rice et al.

(10) Patent No.: US 11,939,557 B2
(45) Date of Patent: Mar. 26, 2024

(54) BETA-GLUCOSIDASE EXPRESSING YEAST FOR ENHANCED FLAVOR AND AROMA IN BEVERAGE PRODUCTION

(71) Applicant: Danstar Ferment AG, Zug (CH)

(72) Inventors: Charles F. Rice, Plainfield, NH (US); Aaron Argyros, Lebanon, NH (US)

(73) Assignee: Danstar Ferment AG, Zug (CH)

( * ) Notice: Subject to any disclaimer, the term of this patent is extended or adjusted under 35 U.S.C. 154(b) by 413 days.

(21) Appl. No.: 17/205,873

(22) Filed: Mar. 18, 2021

(65) Prior Publication Data

US 2021/0292688 A1    Sep. 23, 2021

Related U.S. Application Data

(60) Provisional application No. 62/992,407, filed on Mar. 20, 2020.

(51) Int. Cl.

| C12N 1/16 | (2006.01) |
|---|---|
| C12C 11/09 | (2006.01) |
| C12N 1/18 | (2006.01) |
| C12P 1/02 | (2006.01) |
| C12R 1/865 | (2006.01) |

(52) U.S. Cl.
CPC ............... *C12C 11/09* (2013.01); *C12N 1/16* (2013.01); *C12N 1/185* (2021.05); *C12P 1/02* (2013.01); *C12N 2523/00* (2013.01); *C12R 2001/865* (2021.05)

(58) Field of Classification Search
CPC ............. C12N 1/16; C12N 1/18; C12C 11/09
See application file for complete search history.

(56) References Cited

U.S. PATENT DOCUMENTS

| 9,206,444 B2 | 12/2015 | Brevnova et al. |
| 2016/0002692 A1 | 1/2016 | McBride et al. |

FOREIGN PATENT DOCUMENTS

| WO | 2019/171230 A1 | 9/2019 |
| WO | 2020/058914 A1 | 3/2020 |

OTHER PUBLICATIONS

Daenen et al., "Evaluation of the glycoside hydrolase activity of a *Brettanomyces* strain on glycosides from sour cherry (*Prunus cerasus* L.) used in the production of special fruit beers," *FEMS Yeast Res* 8:1103-1114, 2008.
Daenen, "Use of beta-glucosidase activity for flavour enhancement in specialty beers," Chair De Clerck 2012, 23 pages.
Den Haan et al., "Hydrolysis and fermentation of amorphous cellulose by recombinant *Saccharomyces cerevisiae*," *Metabolic Engineering* 9:87-94, 2007.
Holt et al., "The molecular biology of fruity and floral aromas in beer and other alcoholic beverages," *FEMS Microbiology Reviews* 43:193-222, 2019.
King et al., "Biotransformation of hop aroma terpenoids by ale and lager yeasts," *FEMS Yeast Research* 3:53-62, 2003.
Kirkpatrick, "Optimizing hop aroma in beer dry hopped with Cascade utilizing glycosidic enzymes." Young Scientist Symposium—Chico, CA 2016, 32 pages.
Kollmannsberger et al., "Occurence of glycosidically bound flavor compounds in hops, hop products and beer," *Monatsschrift für Brauwissenschaft*, 2006, 7 pages.
Larue et al., "Directed evolution of a fungal β-glucosidase in *Saccharomyces cerevisiae*," *Biotechnol Biofuels* 9:52, 2016, 15 pages.
Lee et al., "Simultaneous saccharification and fermentation by engineered *Saccharomyces cerevisiae* without supplementing extracellular β-glucosidase," *Journal of Biotechnology* 167:316-322, 2013.
Murai et al., "Assimilation of Cellooligosaccharides by a Cell Surface-Engineered Yeast Expressing β-Glucosidase and Carboxymethylcellulase from *Aspergillus aculeatus*," *Applied and Environmental Microbiology* 64(12):4857-4861, 1998.
Takoi et al., "Biotransformation of Hop-Derived Monoterpene Alcohols by Lager Yeast and Their Contribution to the Flavor of Hopped Beer," *J. Agric. Food Chem.* 58:5050-5058, 2010.
Wilde et al., "Expression of a library of fungal-β-glucosidases in *Saccharomyces cerevisiae* for the development of a biomass fermenting strain," *Appl Microbiol Biotechnol* 95:647-659, 2012.

*Primary Examiner* — Tekchand Saidha
(74) *Attorney, Agent, or Firm* — Seed IP Law Group LLP

(57) ABSTRACT

The present disclosure concerns recombinant yeast host cells expressing heterologous enzymes for hydrolyzing flavor compounds glycosidically bound to a sugar molecule. The recombinant yeast host cells can be used in a subsequent production process to make alcoholic beverage products such as wines and beers.

20 Claims, 8 Drawing Sheets

Specification includes a Sequence Listing.

SEQUENCE LISTING

<160> NUMBER OF SEQ ID NOS: 5

<210> SEQ ID NO 1
<211> LENGTH: 860
<212> TYPE: PRT
<213> ORGANISM: Aspergillus niger
<220> FEATURE:
<221> NAME/KEY: SIGNAL
<222> LOCATION: (1)..(19)

<400> SEQUENCE: 1

Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

-continued

Pro Asn Phe Ser Ser Trp Thr Arg Asp Glu Tyr Gly Tyr Lys Tyr Tyr
        355                 360                 365

Tyr Val Ser Glu Gly Pro Tyr Glu Lys Val Asn Gln Tyr Val Asn Val
    370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Gly Ser Asn Pro Tyr Gly Ala
            420                 425                 430

Asn Gly Cys Ser Asp Arg Gly Cys Asp Asn Gly Thr Leu Ala Met Gly
        435                 440                 445

Trp Gly Ser Gly Thr Ala Asn Phe Pro Tyr Leu Val Thr Pro Glu Gln
    450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
        515                 520                 525

Asn Gly Asp Asn Val Ile Lys Ala Ala Ala Ser Asn Cys Asn Asn Thr
    530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Ser Gly Leu Gln Arg Ile Thr
    690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr

```
                770              775              780
Val Ser Leu Gly Gly Pro Asn Glu Pro Lys Ile Val Leu Arg Gln Phe
785                  790              795                  800

Glu Arg Ile Thr Leu Gln Pro Ser Glu Thr Lys Trp Ser Thr Thr
                805              810              815

Leu Thr Arg Arg Asp Leu Ala Asn Trp Asn Val Glu Lys Gln Asp Trp
            820              825              830

Glu Ile Thr Ser Tyr Pro Lys Met Val Phe Val Gly Ser Ser Ser Arg
            835              840              845

Lys Leu Pro Leu Arg Ala Ser Leu Pro Thr Val His
850              855              860
```

<210> SEQ ID NO 2
<211> LENGTH: 861
<212> TYPE: PRT
<213> ORGANISM: Aspergillus oryzae

<400> SEQUENCE: 2

```
Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285
```

-continued

```
Val Gly Ala Ala Leu Ala Gly Leu Asp Met Ser Met Pro Gly Asp Val
290                 295                 300
Thr Phe Asp Ser Gly Thr Ser Phe Trp Gly Ala Asn Leu Thr Val Gly
305                 310                 315                 320
Val Leu Asn Gly Thr Ile Pro Gln Trp Arg Val Asp Asp Met Ala Val
            325                 330                 335
Arg Ile Met Ala Ala Tyr Tyr Lys Val Gly Arg Asp Thr Lys Tyr Thr
            340                 345                 350
Pro Pro Asn Phe Ser Ser Trp Thr Arg Asp Glu Tyr Gly Phe Ala His
            355                 360                 365
Asn His Val Ser Glu Gly Ala Tyr Glu Arg Val Asn Glu Phe Val Asp
370                 375                 380
Val Gln Arg Asp His Ala Asp Leu Ile Arg Arg Ile Gly Ala Gln Ser
385                 390                 395                 400
Thr Val Leu Leu Lys Asn Lys Gly Ala Leu Pro Leu Ser Arg Lys Glu
            405                 410                 415
Lys Leu Val Ala Leu Leu Gly Glu Asp Ala Gly Ser Asn Ser Trp Gly
            420                 425                 430
Ala Asn Gly Cys Asp Asp Arg Gly Cys Asp Asn Gly Thr Leu Ala Met
            435                 440                 445
Ala Trp Gly Ser Gly Thr Ala Asn Phe Pro Tyr Leu Val Thr Pro Glu
450                 455                 460
Gln Ala Ile Gln Asn Glu Val Leu Gln Gly Arg Gly Asn Val Phe Ala
465                 470                 475                 480
Val Thr Asp Ser Trp Ala Leu Asp Lys Ile Ala Ala Ala Arg Gln
            485                 490                 495
Ala Ser Val Ser Leu Val Phe Val Asn Ser Asp Ser Gly Glu Gly Tyr
            500                 505                 510
Leu Ser Val Asp Gly Asn Glu Gly Asp Arg Asn Asn Ile Thr Leu Trp
            515                 520                 525
Lys Asn Gly Asp Asn Val Val Lys Thr Ala Ala Asn Cys Asn Asn
530                 535                 540
Thr Val Val Ile Ile His Ser Val Gly Pro Val Leu Ile Asp Glu Trp
545                 550                 555                 560
Tyr Asp His Pro Asn Val Thr Gly Ile Leu Trp Ala Gly Leu Pro Gly
            565                 570                 575
Gln Glu Ser Gly Asn Ser Ile Ala Asp Val Leu Tyr Gly Arg Val Asn
            580                 585                 590
Pro Gly Ala Lys Ser Pro Phe Thr Trp Gly Lys Thr Arg Glu Ser Tyr
            595                 600                 605
Gly Ser Pro Leu Val Lys Asp Ala Asn Asn Gly Asn Gly Ala Pro Gln
610                 615                 620
Ser Asp Phe Thr Gln Gly Val Phe Ile Asp Tyr Arg His Phe Asp Lys
625                 630                 635                 640
Phe Asn Glu Thr Pro Ile Tyr Glu Phe Gly Tyr Gly Leu Ser Tyr Thr
            645                 650                 655
Thr Phe Glu Leu Ser Asp Leu His Val Gln Pro Leu Asn Ala Ser Arg
            660                 665                 670
Tyr Thr Pro Thr Ser Gly Met Thr Glu Ala Ala Lys Asn Phe Gly Glu
            675                 680                 685
Ile Gly Asp Ala Ser Glu Tyr Val Tyr Pro Glu Gly Leu Glu Arg Ile
            690                 695                 700
His Glu Phe Ile Tyr Pro Trp Ile Asn Ser Thr Asp Leu Lys Ala Ser
```

```
                705                 710                 715                 720
Ser Asp Asp Ser Asn Tyr Gly Trp Glu Asp Ser Lys Tyr Ile Pro Glu
                    725                 730                 735

Gly Ala Thr Asp Gly Ser Ala Gln Pro Arg Leu Pro Ala Ser Gly Gly
                740                 745                 750

Ala Gly Gly Asn Pro Gly Leu Tyr Glu Asp Leu Phe Arg Val Ser Val
                755                 760                 765

Lys Val Lys Asn Thr Gly Asn Val Ala Gly Asp Glu Val Pro Gln Leu
                770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                    805                 810                 815

Thr Leu Thr Arg Arg Asp Leu Ala Asn Trp Asp Val Ser Ala Gln Asp
                820                 825                 830

Trp Thr Val Thr Pro Tyr Pro Lys Thr Ile Tyr Val Gly Asn Ser Ser
                835                 840                 845

Arg Lys Leu Pro Leu Gln Ala Ser Leu Pro Lys Ala Gln
                850                 855                 860

<210> SEQ ID NO 3
<211> LENGTH: 894
<212> TYPE: PRT
<213> ORGANISM: Saccharomycopsis fibuligera
<220> FEATURE:
<221> NAME/KEY: SIGNAL
<222> LOCATION: (1)..(17)

<400> SEQUENCE: 3

Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
                20                  25                  30

Arg Ser Arg Val Pro Ile Gln Asn Tyr Thr Gln Ser Pro Ser Gln Arg
            35                  40                  45

Asp Glu Ser Ser Gln Trp Val Ser Pro His Tyr Tyr Pro Thr Pro Gln
        50                  55                  60

Gly Gly Arg Leu Gln Asp Val Trp Gln Glu Ala Tyr Ala Arg Ala Lys
65                  70                  75                  80

Ala Ile Val Gly Gln Met Thr Ile Val Glu Lys Val Asn Leu Thr Thr
                85                  90                  95

Gly Thr Gly Trp Gln Leu Asp Pro Cys Val Gly Asn Thr Gly Ser Val
            100                 105                 110

Pro Arg Phe Gly Ile Pro Asn Leu Cys Leu Gln Asp Gly Pro Leu Gly
        115                 120                 125

Val Arg Phe Ala Asp Phe Val Thr Gly Tyr Pro Ser Gly Leu Ala Thr
    130                 135                 140

Gly Ala Thr Phe Asn Lys Asp Leu Phe Leu Gln Arg Gly Gln Ala Leu
145                 150                 155                 160

Gly His Glu Phe Asn Ser Lys Gly Val His Ile Ala Leu Gly Pro Ala
                165                 170                 175

Val Gly Pro Leu Gly Val Lys Ala Arg Gly Gly Arg Asn Phe Glu Ala
            180                 185                 190

Phe Gly Ser Asp Pro Tyr Leu Gln Gly Thr Ala Ala Ala Ala Thr Ile
        195                 200                 205
```

-continued

```
Lys Gly Leu Gln Glu Asn Asn Val Met Ala Cys Val Lys His Phe Ile
    210                 215                 220

Gly Asn Glu Gln Glu Lys Tyr Arg Gln Pro Asp Asp Ile Asn Pro Ala
225                 230                 235                 240

Thr Asn Gln Thr Thr Lys Glu Ala Ile Ser Ala Asn Ile Pro Asp Arg
                245                 250                 255

Ala Met His Ala Leu Tyr Leu Trp Pro Phe Ala Asp Ser Val Arg Ala
                260                 265                 270

Gly Val Gly Ser Val Met Cys Ser Tyr Asn Arg Val Asn Asn Thr Tyr
                275                 280                 285

Ala Cys Glu Asn Ser Tyr Met Met Asn His Leu Leu Lys Glu Glu Leu
    290                 295                 300

Gly Phe Gln Gly Phe Val Val Ser Asp Trp Gly Ala Gln Leu Ser Gly
305                 310                 315                 320

Val Tyr Ser Ala Ile Ser Gly Leu Asp Met Ser Met Pro Gly Glu Val
                325                 330                 335

Tyr Gly Gly Trp Asn Thr Gly Thr Ser Phe Trp Gly Gln Asn Leu Thr
                340                 345                 350

Lys Ala Ile Tyr Asn Glu Thr Val Pro Ile Glu Arg Leu Asp Asp Met
                355                 360                 365

Ala Thr Arg Ile Leu Ala Ala Leu Tyr Ala Thr Asn Ser Phe Pro Thr
370                 375                 380

Glu Asp His Leu Pro Asn Phe Ser Ser Trp Thr Thr Lys Glu Tyr Gly
385                 390                 395                 400

Asn Lys Tyr Tyr Ala Asp Asn Thr Thr Glu Ile Val Lys Val Asn Tyr
                405                 410                 415

Asn Val Asp Pro Ser Asn Asp Phe Thr Glu Asp Thr Ala Leu Lys Val
                420                 425                 430

Ala Glu Glu Ser Ile Val Leu Leu Lys Asn Glu Asn Asn Thr Leu Pro
                435                 440                 445

Ile Ser Pro Glu Lys Ala Lys Arg Leu Leu Leu Ser Gly Ile Ala Ala
    450                 455                 460

Gly Pro Asp Pro Ile Gly Tyr Gln Cys Glu Asp Gln Ser Cys Thr Asn
465                 470                 475                 480

Gly Ala Leu Phe Gln Gly Trp Gly Ser Gly Ser Val Gly Ser Pro Lys
                485                 490                 495

Tyr Gln Val Thr Pro Phe Glu Glu Ile Ser Tyr Leu Ala Arg Lys Asn
                500                 505                 510

Lys Met Gln Phe Asp Tyr Ile Arg Glu Ser Tyr Asp Leu Ala Gln Val
    515                 520                 525

Thr Lys Val Ala Ser Asp Ala His Leu Ser Ile Val Val Val Ser Ala
    530                 535                 540

Ala Ser Gly Glu Gly Tyr Ile Thr Val Asp Gly Asn Gln Gly Asp Arg
545                 550                 555                 560

Lys Asn Leu Thr Leu Trp Asn Asn Gly Asp Lys Leu Ile Glu Thr Val
                565                 570                 575

Ala Glu Asn Cys Ala Asn Thr Val Val Val Thr Ser Thr Gly Gln
                580                 585                 590

Ile Asn Phe Glu Gly Phe Ala Asp His Pro Asn Val Thr Ala Ile Val
                595                 600                 605

Trp Ala Gly Pro Leu Gly Asp Arg Ser Gly Thr Ala Ile Ala Asn Ile
610                 615                 620

Leu Phe Gly Lys Ala Asn Pro Ser Gly His Leu Pro Phe Thr Ile Ala
```

```
            625                 630                 635                 640
Lys Thr Asp Asp Asp Tyr Ile Pro Ile Glu Thr Tyr Ser Pro Ser Ser
                    645                 650                 655
Gly Glu Pro Glu Asp Asn His Leu Val Glu Asn Asp Leu Leu Val Asp
                660                 665                 670
Tyr Arg Tyr Phe Glu Lys Asn Ile Glu Pro Arg Tyr Ala Phe Gly
            675                 680                 685
Tyr Gly Leu Ser Tyr Asn Glu Tyr Glu Val Ser Asn Ala Lys Val Ser
            690                 695                 700
Ala Ala Lys Lys Val Asp Glu Glu Leu Pro Glu Pro Ala Thr Tyr Leu
705                 710                 715                 720
Ser Glu Phe Ser Tyr Gln Asn Ala Lys Asp Ser Lys Asn Pro Ser Asp
                725                 730                 735
Ala Phe Ala Pro Ala Asp Leu Asn Arg Val Asn Glu Tyr Leu Tyr Pro
                740                 745                 750
Tyr Leu Asp Ser Asn Val Thr Leu Lys Asp Gly Asn Tyr Glu Tyr Pro
            755                 760                 765
Asp Gly Tyr Ser Thr Glu Gln Arg Thr Thr Pro Asn Gln Pro Gly Gly
            770                 775                 780
Gly Leu Gly Gly Asn Asp Ala Leu Trp Glu Val Ala Tyr Asn Ser Thr
785                 790                 795                 800
Asp Lys Phe Val Pro Gln Gly Asn Ser Thr Asp Lys Phe Val Pro Gln
                805                 810                 815
Leu Tyr Leu Lys His Pro Glu Asp Gly Lys Phe Glu Thr Pro Ile Gln
                820                 825                 830
Leu Arg Gly Phe Glu Lys Val Glu Leu Ser Pro Gly Glu Lys Lys Thr
            835                 840                 845
Val Asp Leu Arg Leu Leu Arg Arg Asp Leu Ser Val Trp Asp Thr Thr
        850                 855                 860
Arg Gln Ser Trp Ile Val Glu Ser Gly Thr Tyr Glu Ala Leu Ile Gly
865                 870                 875                 880
Val Ala Val Asn Asp Ile Lys Thr Ser Val Leu Phe Thr Ile
                885                 890

<210> SEQ ID NO 4
<211> LENGTH: 841
<212> TYPE: PRT
<213> ORGANISM: Brettanomyces anomalus

<400> SEQUENCE: 4

Met Thr Phe Asp Val Asp Ser Ile Leu Gly Gln Leu Thr Glu Glu
1               5                   10                  15
Lys Val Ser Leu Ile Ala Ala Val Asp Asn Trp His Thr Lys Glu Ile
                20                  25                  30
Lys Arg Leu Asp Ile Pro Ala Ile Arg Val Ser Asp Gly Pro Asn Gly
            35                  40                  45
Ile Arg Gly Thr Arg Phe Phe Asn Gly Val Pro Ser Ala Cys Phe Pro
        50                  55                  60
Asn Gly Thr Gly Leu Ala Ala Thr Phe Asp Ala Asp Leu Leu Glu Lys
65                  70                  75                  80
Ala Gly Glu Leu Met Ser Ile Glu Ala Glu His Lys Asn Ala Gln Val
                85                  90                  95
Ile Leu Gly Pro Thr Thr Asn Ile Gln Arg Gly Pro Leu Gly Gly Arg
            100                 105                 110
```

```
Gly Phe Glu Ser Phe Ser Glu Asp Pro Phe Leu Ser Gly Ile Cys Thr
            115                 120                 125
Ala Ser Ile Val Asn Gly Ile Gln Lys Ser Gly Lys Ile Gly Ala Thr
        130                 135                 140
Val Lys His Phe Val Cys Asn Asp Leu Glu Asp Gln Arg Phe Ser Ser
145                 150                 155                 160
Asn Ser Val Leu Thr Gln Arg Ala Leu Arg Glu Ile Tyr Leu Glu Pro
                165                 170                 175
Phe Arg Leu Ala Val Lys Leu Ala Asp Pro Lys Cys Phe Met Thr Ser
            180                 185                 190
Tyr Asn Lys Val Asn Asp Glu His Cys Ser Gln Asn Tyr His Leu Ile
        195                 200                 205
Glu Glu Ile Leu Arg Gly Glu Trp Asn Trp Lys Gly Met Ile Met Ser
        210                 215                 220
Asp Trp Phe Gly Thr Tyr Ser Thr Ala Ala Ala Leu Lys His Gly Ile
225                 230                 235                 240
Asp Ile Glu Phe Pro Gly Pro Thr Lys Phe Arg Arg Trp Glu Val Val
                245                 250                 255
Lys His Leu Leu Gln Ser Lys Glu Ala Asp Leu Lys Glu Asp Ile
            260                 265                 270
Asp Asn Arg Cys Arg Asn Val Leu Lys Leu Ile Lys Phe Val Val Asp
        275                 280                 285
Thr Arg Gly Asn Gly Pro Tyr Pro Thr Ala Glu Asp Thr Lys Asn Asp
        290                 295                 300
Thr Pro Glu Thr Ser Ala Lys Leu Arg Asn Leu Ala Ala Gln Gly Ile
305                 310                 315                 320
Val Leu Leu Lys Asn Asp Arg Gly Val Leu Pro Leu Ser Lys Asp Lys
                325                 330                 335
Ser Thr Val Val Ile Gly Pro Asn Gly Lys Ala Leu Asn Thr Ile Ser
            340                 345                 350
Gly Gly Gly Ser Ala Ser Met Arg Pro Tyr His Val Val Thr Pro Tyr
        355                 360                 365
Asp Gly Ile Lys Ser Lys Val Gly Lys Val Asp Tyr Thr Val Gly Cys
        370                 375                 380
Tyr Cys Asp Lys Ala Leu Lys Asn Leu Phe Glu Phe Met Thr Asn Asp
385                 390                 395                 400
Leu Asp Lys Ser Lys Lys Gly Val Lys Ala Thr Phe Tyr Thr Lys Ala
                405                 410                 415
Phe Glu Asn Arg Asp Ala Ser Lys Pro Ile Asp Glu Met Ile Val
            420                 425                 430
Asp Ser Ser Phe Val Thr Leu Phe Asp Tyr Ser Asn Pro Ala Val Asp
        435                 440                 445
Ser Glu Lys Lys Leu Phe Tyr Val Asp Phe Glu Gly Tyr Tyr Thr Pro
        450                 455                 460
Asp Ala Thr Ala Asp Tyr Lys Phe Gly Cys Gln Val Phe Gly Thr Ala
465                 470                 475                 480
Leu Val Tyr Val Asp Gly Lys Leu Leu Ile Asp Asn Lys Thr Ser Gln
                485                 490                 495
Thr Lys Gly Thr Phe Cys Phe Ser Gly Thr Val Glu Glu Thr Ala
            500                 505                 510
Val Thr His Leu Glu Ala Gly His Ser Tyr Lys Ile Lys Val Glu Phe
        515                 520                 525
Gly Ser Gly Ile Thr Ser Lys Ile Ser Ser Asp Phe Gly Ser Gly Gly
```

```
                530             535             540
Leu Gln Val Gly Ile Thr Lys Val Ile Asp Pro Glu Ile Glu Val Glu
545                 550                 555                 560

His Ala Ala Glu Leu Ala Lys Ser His Asp Asn Val Ile Leu Cys Ile
                565                 570                 575

Gly Leu Asn Gly Glu Trp Glu Ser Glu Gly Tyr Asp Arg Ala Asp Met
                580                 585                 590

Thr Leu Pro Gly Lys Thr Asn Asp Leu Val Ser Ala Val Leu Lys Ala
                595                 600                 605

Asn Pro Asn Thr Val Ile Val Asn Gln Ser Gly Thr Pro Val Glu Met
                610                 615                 620

Pro Trp Leu Gly Glu Ser His Thr Leu Leu Gln Ala Trp Tyr Gly Gly
625                 630                 635                 640

Asn Glu Met Gly Asp Ala Leu Ala Asp Ile Leu Phe Gly Asp Ala Val
                645                 650                 655

Pro Ser Gly Lys Leu Ser Leu Ser Trp Pro Phe Lys Asn Gln Asp Asn
                660                 665                 670

Pro Ala Tyr Leu Asn Phe Ser Thr Glu Met Gly Arg Val Leu Tyr Gly
                675                 680                 685

Glu Asp Val Phe Val Gly Tyr Arg Tyr Tyr Glu Lys Leu Gln Arg Arg
690                 695                 700

Val Ala Phe Pro Phe Gly Tyr Gly Leu Ser Tyr Thr Thr Phe Lys Phe
705                 710                 715                 720

Asp Asp Leu Lys Val Ser Ser Asp Asn Thr Asn Val Thr Val Ser Phe
                725                 730                 735

Thr Val Lys Asn Thr Gly Asp Lys Tyr Thr Ala Lys Glu Val Thr Gln
                740                 745                 750

Leu Tyr Ile Ser Ala Val Glu Ser Ser Val Thr Arg Pro Val Lys Glu
                755                 760                 765

Leu Lys Ala Phe Ala Lys Pro Glu Leu Lys Pro Gly Glu Ser Lys Thr
                770                 775                 780

Val Ser Phe Asn Leu Ser Leu Glu Asp Ala Cys Ser Phe Phe Asp Glu
785                 790                 795                 800

Tyr Arg Asn Lys Trp Cys Leu Glu Ala Gly Lys Tyr Glu Ala Gln Val
                805                 810                 815

Gly Ser Ser Ser Asp Asp Ile His Leu Ile Gly Glu Phe Asp Val Ala
                820                 825                 830

Lys Thr Val Tyr Phe Val Arg Ser Ala
                835                 840

<210> SEQ ID NO 5
<211> LENGTH: 840
<212> TYPE: PRT
<213> ORGANISM: Brettanomyces bruxellensis

<400> SEQUENCE: 5

Met Ile Phe Asp Val Glu Asn Thr Leu Arg Asp Leu Thr Thr Glu Glu
1               5                   10                  15

Lys Val Ser Leu Leu Ser Ala Ser Asp Phe Trp His Thr Ser Ser Ile
                20                  25                  30

Glu Arg Leu Asn Ile Pro Phe Ile Arg Val Ser Asp Gly Pro Asn Gly
                35                  40                  45

Ile Arg Gly Thr Lys Phe Phe Asn Gly Val Pro Ser Ala Cys Phe Pro
                50                  55                  60
```

```
Asn Gly Thr Gly Leu Ala Ser Thr Phe Asp Cys Asp Leu Leu Glu Glu
 65                  70                  75                  80

Ile Gly Glu Leu Met Ala Val Glu Ala Lys His Lys Gly Ala Gln Ile
                 85                  90                  95

Ile Leu Gly Pro Thr Thr Asn Ile Leu Arg Gly Pro Leu Gly Gly Arg
            100                 105                 110

Gly Phe Glu Ser Phe Ser Glu Asp Pro Val Leu Ser Gly Leu Cys Thr
        115                 120                 125

Ala Ala Ile Val Lys Gly Ile Gln Asn Asp Gly Arg Ile Cys Ala Thr
    130                 135                 140

Val Lys His Phe Val Cys Asn Asp Leu Glu His Glu Arg Leu Ser Ser
145                 150                 155                 160

Asn Ser Val Val Ser Glu Arg Ala Leu Arg Glu Ile Tyr Leu Glu Pro
                165                 170                 175

Phe Arg Ile Ala Val Gln Leu Ala Asn Pro Ile Cys Ile Met Thr Ala
            180                 185                 190

Tyr Asn Lys Val Asn Gly Ile His Cys Ser Glu Asn Tyr Gln Leu Ile
        195                 200                 205

Glu Asn Ile Leu Arg Lys Glu Trp Asn Trp Asp Gly Leu Leu Met Ser
    210                 215                 220

Asp Trp Phe Gly Thr Tyr Ser Thr Leu Asn Ser Leu Lys His Gly Ile
225                 230                 235                 240

Asp Ile Glu Phe Pro Gly Pro Ser Gln Phe Arg Arg Trp Asp Thr Ile
                245                 250                 255

Lys His Leu Leu Gln Ser Lys Ala Asp Asn Leu Lys Gln Thr Asp Ile
            260                 265                 270

Asp Asn His Cys Arg His Ile Leu Lys Val Ile Lys Ser Leu Ile Glu
        275                 280                 285

Ser Asn Gly Thr Thr Leu Phe Ser Lys Val Glu Asp Ser Leu Asn Asp
    290                 295                 300

Lys Pro Glu Thr Ser Glu Lys Leu Arg Arg Ala Ala Glu Gly Ile
305                 310                 315                 320

Val Leu Leu Lys Asn Glu Arg Lys Val Leu Pro Leu Leu Lys Glu Thr
                325                 330                 335

Pro Val Leu Val Ile Gly Pro Asn Ala Ile Ser Leu Asn Thr Tyr Ser
            340                 345                 350

Gly Gly Gly Ser Ala Ser Leu Thr Pro Tyr His Ile Val Thr Pro Leu
        355                 360                 365

Gln Gly Ile Lys Lys Ala Ser Lys Val Glu Phe Thr Ile Gly Ala
    370                 375                 380

His Ser His Lys Ala Leu Gly Gly Leu Phe Glu Lys Met Thr Asn Asp
385                 390                 395                 400

Leu Glu Lys Phe Glu Asn Gly Val Arg Ala Arg Phe Tyr Thr Lys Pro
                405                 410                 415

Arg Glu Lys Arg Leu Lys Glu Asp Lys Pro Ile Asp Glu Met Ile Ile
            420                 425                 430

Lys Asn Ser Tyr Val Thr Leu Phe Asp Tyr Thr Asn Pro Ala Val Asn
        435                 440                 445

Gln Glu Ser Lys Leu Phe Tyr Ala Asp Phe Glu Gly Tyr Tyr Thr Pro
    450                 455                 460

Thr Glu Ser Gly Asp Tyr Gln Ile Gly Cys Gln Val Ala Gly Thr Ala
465                 470                 475                 480

Ile Val Tyr Ile Asp Asp Lys Ile Leu Ile Asp Asn Lys Thr Lys Gln
```

```
                        485                 490                 495
Thr Lys Gly Thr Phe Cys Phe Ser Gly Gly Thr Ile Glu Glu Thr Ala
                500                 505                 510

Cys Ile Tyr Met Gln Ala Tyr Gln Lys Tyr Arg Ile Lys Val Glu Phe
            515                 520                 525

Gly Ser Gly Ile Thr Ser Lys Ile Tyr Thr Asn Phe Gly Ala Gly Gly
        530                 535                 540

Leu Gln Val Gly Ile Thr Lys Val Ile Asp Pro Gln Lys Glu Ile Lys
545                 550                 555                 560

Lys Ala Ala Ser Leu Ala Ala Ser Tyr Gln Asn Val Ile Leu Cys Ile
                565                 570                 575

Gly Leu Asn Ser Glu Trp Glu Ser Glu Gly Tyr Asp Arg Glu Asp Met
                580                 585                 590

Lys Leu Pro Gly Arg Thr Asp Asp Leu Val Arg Ala Val Ile Gln Ala
            595                 600                 605

Asn Pro Asn Thr Val Val Ile Asn Gln Ser Gly Thr Pro Val Glu Met
            610                 615                 620

Pro Trp Leu Asp Gln Cys Asp Thr Leu Leu Gln Thr Trp Tyr Gly Gly
625                 630                 635                 640

Asp Glu Leu Gly Asp Ala Val Ala Asp Ile Leu Tyr Gly Asp Thr Ile
                645                 650                 655

Pro Cys Gly Lys Leu Pro Phe Ser Trp Pro Ala Lys Asn Glu Asp Asn
                660                 665                 670

Pro Ser Phe Leu Asn Phe Arg Thr Glu Lys Gly Arg Val Leu Tyr Gly
            675                 680                 685

Glu Asp Val Tyr Val Gly Tyr Arg Tyr Tyr Glu Lys Leu His Arg Asn
690                 695                 700

Val Ala Phe Pro Phe Gly Tyr Gly Leu Ser Tyr Thr Gln Phe Glu Tyr
705                 710                 715                 720

Gln Asn Leu Lys Val Ser Ser Asp Ser Asn Asn Leu Ile Leu Ser Phe
                725                 730                 735

Glu Ile Lys Asn Ile Gly Gln Tyr Ala Gly Lys Glu Thr Ala Gln Val
            740                 745                 750

Tyr Ile Ser Ser Leu Gly Pro Thr Ile Ser Arg Pro Ser Lys Glu Leu
            755                 760                 765

Lys Ala Phe Met Lys Thr Thr Leu Glu Pro Gly Glu Ser Lys Val Met
            770                 775                 780

Asn Phe Arg Leu Lys Phe Lys Glu Ile Cys Ser Tyr Tyr Asp Glu Tyr
785                 790                 795                 800

Gln Lys Met Trp Cys Leu Glu Ser Gly Lys Tyr Leu Ala Leu Val Gly
                805                 810                 815

Ala Ser Ser Met Asn Ile Ser Leu Thr Gly Ser Phe Asp Ile Leu Glu
                820                 825                 830

Thr Thr Tyr Phe Glu Lys Arg Cys
                835                 840
```

BETA-GLUCOSIDASE EXPRESSING YEAST FOR ENHANCED FLAVOR AND AROMA IN BEVERAGE PRODUCTION

CROSS-REFERENCE TO RELATED APPLICATION AND STATEMENT REGARDING SEQUENCE LISTING

The present application claims priority from U.S. provisional application 62/992,407 filed on Mar. 20, 2020 and herewith incorporated in its entirety. The sequence listing associated with this application is provided in text format in lieu of a paper copy and is hereby incorporated by reference into the specification. The name of the text file containing the sequence listing is 240141_406_SEQUENCE_LISTING. The text file is 36.4 KB, was created on Mar. 17, 2021 and is being submitted electronically via EFS-Web.

TECHNOLOGICAL FIELD

The present disclosure relates to a recombinant yeast host cell expressing beta-glucosidase for making a fermented beverage.

BACKGROUND

Beer and wine are complex media with flavor, aroma and color all being important characteristics. In beer, all four of the primary ingredients (water, yeast, hops, and barley) contribute to these complexities, but hops may be the most intricate ingredient as they provide both the main bittering agent, which counters the sweetness of the malt sugars, and infuses the characteristic floral and citrus aromatics. Hops were originally used as a preservative for beer, preventing spoilage during export.

In the United States, the craft industry represents a significant volume share of beer sales, and there are over 6,000 craft breweries leading to an increased demand for the aforementioned raw materials. Coupled with an 80% increase in hop usage by beer production over the past 10 years, the increasing hop demand has led to a corresponding increase in hop prices, which equates to a 20% cost increase in just the last 5 years. There is also a noticeable increase in the use of aroma varieties such as Citra, Simcoe, Amarillo, and Mosaic, all of which have entered the top seven in terms of popularity and volume. However, comparatively speaking, these particular varieties tend to be lower yielding which further increases cost and potential supply shortfalls.

The raw materials associated with brewing, particularly the price of hops, can restrict brewers from purchasing expensive enzyme products. Brewers have used non-*Saccharomyces* strains for their ability to biotransform hops and fruits, such as *Brettanomyces*; however, these organisms produce a number of additional flavor compounds that are undesirable in most beer styles.

It would be desirable to reduce costs and maximize the flavor profile of fermented beverages by improving the conversion of raw materials, and improving release of volatile flavor compounds (such as glycosides) desired for fermented beverage production (in beer and wine for example).

SUMMARY

The present disclosure concerns a recombinant yeast host cell for improving a flavor profile of a fermented beverage by hydrolyzing a non-volatile conjugate comprising a flavorful and volatile compound.

According to a first aspect, the present disclosure concerns a recombinant yeast host cell for improving a flavor profile of a fermented beverage (obtained by fermentation of a fermentable medium with the recombinant yeast host cell) by hydrolyzing a non-volatile conjugate of formula (I):

$$\text{VFC—SM} \qquad (I)$$

where: VFC is a flavor compound that is volatile when released from the non-volatile conjugate, SM is a sugar molecule, "—" is a β-glycosidic linkage covalently attaching the VFC to the SM, and capable of being hydrolyzed. In the context of the present disclosure, the recombinant yeast host cell has a heterologous nucleic acid molecule encoding one or more heterologous polypeptide having 1,4-β-glucosidase activity for hydrolyzing the β-glycosidic linkage to release the VFC from the non-volatile conjugate; has a native ethanol production pathway; and is a brewing or wine strain. In one embodiment, the heterologous polypeptide is a secreted polypeptide. In another embodiment, the heterologous polypeptide is a cell-associated polypeptide. In one embodiment, the membrane-associated polypeptide is a tethered heterologous polypeptide. In one embodiment, the glycosidically-bound VFC is a terpenoid. In one embodiment, the terpenoid is a monoterpene alcohol. In one embodiment, the non-volatile conjugate is a terpene glycoside. In one embodiment, the non-volatile conjugate is from a hop. In one embodiment, the heterologous polypeptide having 1,4-β-glucosidase activity has an amino acid sequence of SEQ ID NO: 1, 2, 3, 4, or 5, is a variant of the amino acid sequence of SEQ ID NO: 1, 2, 3, 4, or 5 having 1,4-β-glucosidase activity or is a fragment thereof of the amino acid sequence of SEQ ID NO: 1, 2, 3, 4, or 5 having 1,4-β-glucosidase activity. In an embodiment, the heterologous polypeptide having 1,4-β-glucosidase activity has the amino acid sequence corresponding to positions 20 to 860 of SEQ ID NO: 1, is a variant of the amino acid sequence corresponding to positions 20 to 860 of SEQ ID NO: 1 having 1,4-β-glucosidase activity or is a fragment of the amino acid sequence corresponding to positions 20 to 860 of SEQ ID NO: 1 having 1,4-β-glucosidase activity. In another embodiment, the heterologous polypeptide having of having 1,4-β-glucosidase activity has the amino acid sequence of SEQ ID NO: 2, is a variant of the amino acid sequence of SEQ ID NO: 2 having 1,4-β-glucosidase activity or is a fragment of the amino acid sequence of SEQ ID NO: 2 having 1,4-β-glucosidase activity. In an embodiment, the heterologous polypeptide having 1,4-β-glucosidase activity has the amino acid sequence corresponding to positions 18 to 876 of SEQ ID NO: 3, is a variant of the amino acid sequence corresponding to positions 18 to 876 of SEQ ID NO: 3 having 1,4-β-glucosidase activity or is a fragment of the amino acid sequence corresponding to positions 18 to 876 of SEQ ID NO: 3 having 1,4-β-glucosidase activity. In another embodiment, the heterologous polypeptide having of having 1,4-β-glucosidase activity has the amino acid sequence of SEQ ID NO: 4, is a variant of the amino acid sequence of SEQ ID NO: 4 having 1,4-β-glucosidase activity or is a fragment of the amino acid sequence of SEQ ID NO: 4 having 1,4-β-glucosidase activity. In another embodiment, the heterologous polypeptide having of having 1,4-β-glucosidase activity has the amino acid sequence of SEQ ID NO: 5, is a variant of the amino acid sequence of SEQ ID NO: 5 having 1,4-β-glucosidase activity or is a fragment of the amino acid sequence of SEQ ID NO: 5 having 1,4-β-glucosidase activity. In one embodiment, the fermentable carbohydrates of the fermentable medium comprises a majority, in weight, of maltose and/or maltotriose. In one embodiment, the recombinant yeast host cell expresses a maltotriose transporter. In one embodiment, the maltotriose transporter is AGT1, a variant thereof or a fragment thereof. In an embodiment, the recombinant yeast host is capable of accumulating or accumulates at least 5 g/L of ethanol during the fermentation. In one embodiment, the recombinant yeast host cell is from the genus *Saccharomyces* sp. In one embodiment, the recombinant yeast host cell is from the species *Saccharomyces cerevisiae* or from the species *Saccharomyces pastorianus*.

According to a second aspect, the present disclosure provides a process for a composition the recombinant yeast host cell described herein and an emulsifier.

According to a third aspect, the present disclosure provides a process for making a fermented beverage from a fermentable medium comprising fermentable carbohydrates and the non-volatile conjugate of formula (I) as described herein, the process comprising contacting the recombinant yeast host cell described herein with the fermentable medium under conditions to allow the hydrolysis of the β-glycosidic linkages during and/or after the conversion of at least some of the fermentable carbohydrates into ethanol by the recombinant yeast host cell. In the context of the present disclosure, the fermentable medium comprises the non-volatile conjugate prior to the addition of the recombinant yeast host cell or composition and/or the fermentable medium is supplemented with the non-volatile conjugate at the same time or after the addition of the recombinant yeast host cell or composition. In an embodiment, the contacting step occurs, at least in part, at a temperature below about 28° C. In another embodiment, the contacting step occurs, at least in part, at a temperature between about 3 and about 28° C. In one embodiment, the process comprises supplementing the fermentable medium with a hop before, during, and/or after the contacting step. In one embodiment, the non-volatile conjugate is derived from the hop. In one embodiment, the process further comprises boiling the fermentable medium together with the hop. In other embodiments, the process comprises adding the hop to the fermentable medium after boiling. In one embodiment, the fermented beverage is beer. In one embodiment, the beer is ale. In one embodiment, the contacting step occurs, at least in part, at a temperature between about 15 and about 24° C. In one embodiment, the beer is lager. In one embodiment, the contacting step occurs, at least in part, at a temperature between about 3 and about 15° C. In one embodiment, the fermentable medium comprises a majority of maltose and/or maltotriose. In one embodiment, the fermented beverage is wine. In one embodiment, the contacting step occurs, at least in part, at a temperature between about 12 and about 28° C. In one embodiment, the fermentable medium comprises glucose, fructose, sucrose, or combinations thereof. In one embodiment, the fermented beverage is distilled spirit.

According to a fourth aspect, the present disclosure provides a beverage obtainable or obtained by the process described herein.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION

Figure 1:
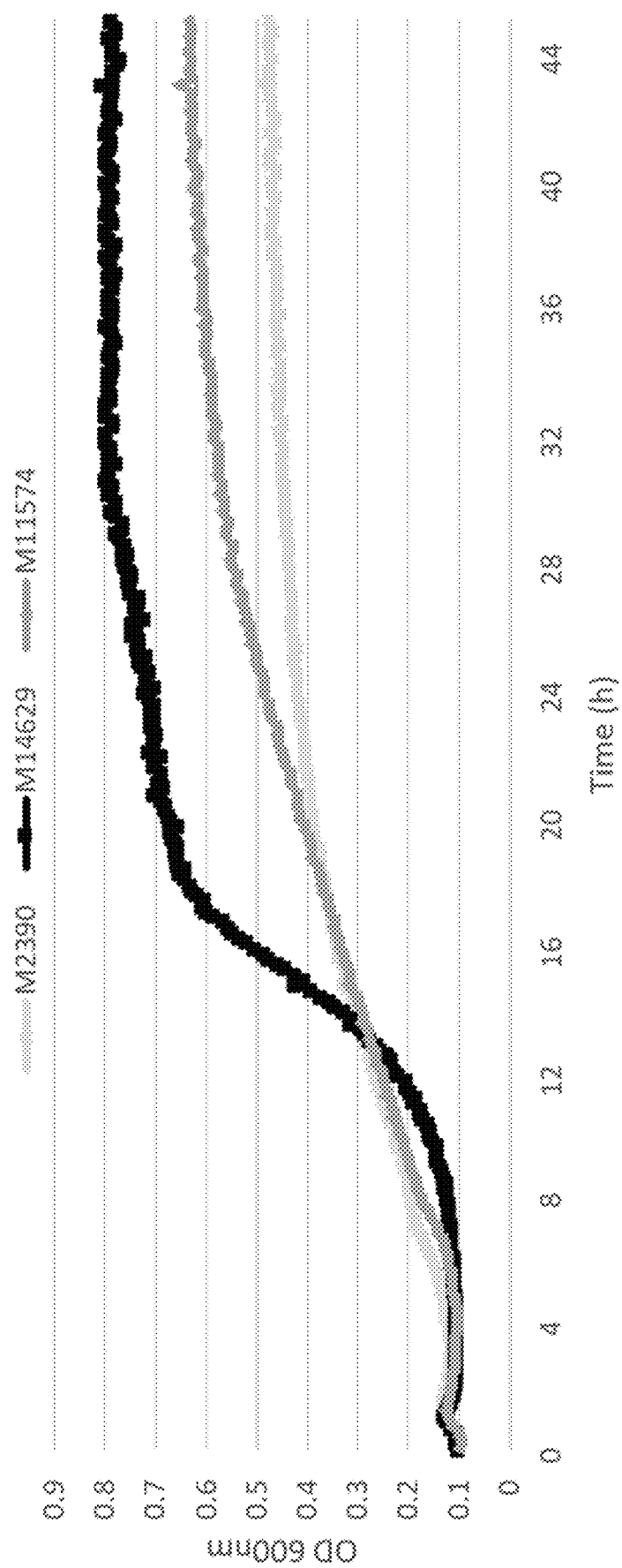
FIG. 1 shows a comparison of the growth of a biofuel strain (M2390—light grey line), a brewing strain (M14629—black line), and a wine strain (M11574—dark grey line) on YP-maltotriose media (10 g/L yeast extract, 20 g/L peptone, 10 g/L maltotriose). Y axis is the absorbance read at a 600 nm wavelength. X axis is time in hours.

The present disclosure provides recombinant yeast host cells for enhancing the flavor and/or aroma of an alcoholic beverage by facilitating the conversion of flavor compound precursors (e.g., volatile flavor compounds bonded via a β-glycosidic linkage to a sugar molecule) to release compounds associated with flavor and/or aroma of an alcoholic fermented beverage. These compounds, which can be essential oils, contribute to aromatics of beer as well as wine. In embodiments involving beer, often times beer brewers are forced to add excessive amounts of hops to obtain desired organoleptic properties due to the low conversion of the precursors into the flavorful compound. Very often, these essential oils are bound to sugars, which are called hop glycosides, and are odorless and non-volatile until they are released from the sugar molecule (to become volatile and flavorful).

Alpha acid resin of hops is the main bittering agent in beer, which is insoluble in water until it is isomerized by boiling the hops together with raw materials. Therefore, the longer the hops are boiled, the greater percentage of isomerization and the more bitter the resulting beer. Hops are also added when brewing beer to extract essential oils which influence flavor and aroma. Whereas hops typically contain 2-20% alpha acids, they contain less than 0.5% essential oils. However, these essentials oils, once released from the hop glycosides, are very volatile, and are therefore evaporated away during the boiling. In some embodiments referred to as "dry hopping", hops are added after boiling or during fermentation to prevent evaporation of the essential oils.

These compounds or essential oils can also be found conjugated to sugar-moieties to form non-volatile, flavorless and odorless compounds. The conjugations occurred naturally in the plant and are present in the hop. As used herein, the expression "a non-volatile conjugate" refers to such conjugated compounds or flavor compound precursors having formula (I):

VFC—SM  (I)

where VFC is a flavor compound that is volatile when released from the conjugate, SM is a sugar molecule, and — is a β-glycosidic linkage covalently attaching the VFC to the SM. The β-glycosidic linkage can be hydrolyzed by enzymes such as glucosidases. Since the volatile flavor compound is bound to a sugar molecule by one or more β-glycosidic linkages, they are considered non-volatile. Non-volatile compounds of formula (I) include, but are not limited to, hop glycosides, terpenoids (such as, for example, monoterpene alcohol and/or terpene glycoside), and terpene glycosides. Non-volatile compounds can be a mixture of distinct non-volatile compounds of formula (I). These compounds, in their conjugated form, are not perceivable to taste or odor but are precursors which release flavor and odor compounds if liberated either thermally or enzymatically.

The present disclosure thus provides a recombinant yeast host cell capable of hydrolyzing the β-glycosidic linkages of non-volatile conjugates, thereby releasing the volatile flavor compounds (VFC) and improving a flavor and aromatic profile of a fermented beverage. As used herein, "β-glycosidic linkages" include (1->4) β-glycosidic linkages. Cleavage of the sugar moiety via β-glucosidases releases flavor compounds from the bound sugar molecules. To hydrolyze the β-glycosidic linkages, the present disclosure provides recombinant yeast host cells expressing one or more heterologous polypeptide having 1,4-β-glucosidase activity which is capable, under the appropriate conditions, of releasing the volatile flavor compound from the sugar molecule.

As used herein, "flavor/flavorful compounds" or "volatile flavor compounds (VFC)" refer to compounds capable of triggering the olfactory receptors of mammals, and includes for example, monoterpene alcohols, linalool, geraniol, β-citronellol, nerol, and α-terpineol.

In the context of the compounds of Formula (I), a sugar molecule (SM) includes, but is not limited to, monosaccharide or polysaccharide pentose or hexose sugar moieties, such as glucose for example.

Polypeptide Having 1,4-β-glucosidase Activity

In the present disclosure, the recombinant yeast host cells have a heterologous nucleic acid molecule encoding one or more heterologous polypeptide having 1,4-β-glucosidase activity. Polypeptides having 1,4-β-glucosidase activity are enzymes that are capable of hydrolyzing or cleaving β-glycosidic linkages, particularly (1->4) β-glycosidic linkages, which bond a flavor compound to a sugar molecule. β-glucosidases catalyze the hydrolysis of the glycosidic bonds to terminal non-reducing residues in beta-D-glucosides and oligosaccharides. Glycosidases (EC 3.2.1) are known as enzymes capable of hydrolyzing O- and S-glycosyl compounds. Glycosidases capable of hydrolyzing a 1-4-β-glycosidic linkage include, but are not limited to, glucan 1,4-β-glucosidase (EC 3.2.1.74).

The term "heterologous" when used in reference to a nucleic acid molecule (such as a promoter or a coding sequence) or a polypeptide refers to a nucleic acid molecule that is not natively found in the recombinant host cell or a polypeptide that is not natively expressed in the recombinant host cell. "Heterologous" also includes a native coding region, or portion thereof, that is removed from the source organism and subsequently reintroduced into the source organism in a form that is different from the corresponding native gene, e.g., not in its natural location in the organism's genome. The heterologous nucleic acid molecule is purposively introduced into the recombinant host cell. The term "heterologous" as used herein also refers to an element (nucleic acid or polypeptide) that is derived from a source other than the endogenous source. Thus, for example, a heterologous element could be derived from a different strain of host cell, or from an organism of a different taxonomic group (e.g., different kingdom, phylum, class, order, family genus, or species, or any subgroup within one of these classifications).

When expressed in the recombinant yeast host cells, the heterologous polypeptides described herein can be encoded on one or more heterologous nucleic acid molecules. The term "heterologous" when used in reference to a nucleic acid molecule (such as a promoter, a terminator or a coding sequence) or a polypeptide refers to a nucleic acid molecule or a polypeptide that is not natively found in the recombinant host cell. "Heterologous" also includes a native coding region/promoter/terminator, or portion thereof, that was removed from the source organism and subsequently reintroduced into the source organism in a form that is different from the corresponding native gene, e.g., not in its natural location in the organism's genome. The heterologous nucleic acid molecule is purposively introduced into the recombinant yeast host cell. For example, a heterologous element could be derived from a different strain of host cell, or from an organism of a different taxonomic group (e.g., different kingdom, phylum, class, order, family genus, or species, or any subgroup within one of these classifications). As used herein, the term "native" when used in inference to a gene, polypeptide, enzymatic activity, or pathway refers to an unmodified gene, polypeptide, enzymatic activity, or pathway originally found in the recombinant host cell. In some embodiments, heterologous polypeptides derived from a different strain of host cell, or from an organism of a different taxonomic group (e.g., different kingdom, phylum, class, order, family genus, or species, or any subgroup within one of these classifications) can be used in the context of the present disclosure.

The heterologous nucleic acid molecule of the present disclosure comprises a coding region for the heterologous polypeptide. A DNA or RNA "coding region" is a DNA or RNA molecule (preferably a DNA molecule) which is transcribed and/or translated into a heterologous polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell (such as the recombinant yeast host cell of the present disclosure), a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

The heterologous nucleic acid molecule described herein can comprise transcriptional and/or translational control regions. "Transcriptional and translational control regions" are DNA regulatory regions, such as promoters, enhancers, terminators, and the like, that provide for the expression of a coding region in a recombinant host cell. In eukaryotic cells, polyadenylation signals are considered control regions.

In some embodiments, the heterologous nucleic acid molecule of the present disclosure includes a promoter as well as a coding sequence for a heterologous polypeptide. The heterologous nucleic acid sequence can also include a terminator. In the heterologous nucleic acid molecules of the present disclosure, the promoter and the terminator (when present) are operatively linked to the nucleic acid coding sequence of the heterologous polypeptide, e.g., they control the expression and the termination of expression of the nucleic acid sequence encoding the heterologous polypeptide. The heterologous nucleic acid molecule of the present disclosure can also include a nucleic acid coding for a signal sequence, e.g., a short peptide sequence for exporting the heterologous polypeptide outside the host cell. When present, the nucleic acid sequence coding for the signal sequence is directly located upstream and in frame of the nucleic acid sequence coding for the heterologous polypeptide. In some embodiments, the signal sequence can be native to the heterologous protein. In additional embodiments, the signal sequence can be heterologous to the heterologous protein.

In the heterologous nucleic acid molecule described herein, the promoter and the nucleic acid molecule coding for the heterologous polypeptide are operatively linked to one another. In the context of the present disclosure, the expressions "operatively linked" or "operatively associated" refers to fact that the promoter is physically associated to the nucleotide acid molecule coding for the heterologous polypeptide in a manner that allows, under certain conditions, for expression of the heterologous polypeptide from the nucleic acid molecule. In an embodiment, the promoter can be located upstream (5') of the nucleic acid sequence coding for the heterologous polypeptide. In still another embodiment, the promoter can be located downstream (3') of the nucleic acid sequence coding for the heterologous polypeptide. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the heterologous polypeptide. The promoters can be located, in view of the nucleic acid molecule coding for the heterologous polypeptide, upstream, downstream as well as both upstream and downstream.

"Promoter" refers to a DNA fragment capable of controlling the expression of a coding sequence or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase.

The promoter can be native or heterologous to the nucleic acid molecule encoding the heterologous polypeptide. The promoter can be heterologous or derived from a strain being from the same genus or species as the recombinant host cell. In an embodiment, the promoter is derived from the same genus or species of the yeast host cell and the heterologous polypeptide is derived from a different genus than the host cell. The promoter can be a single promotor or a combination of different promoters.

In the context of the present disclosure, the promoter controlling the expression of the heterologous polypeptide can be a constitutive promoter (such as, for example, tef2p (e.g., the promoter of the tef2 gene), cwp2p (e.g., the promoter of the cwp2 gene), ssa1p (e.g., the promoter of the ssa1 gene), eno1p (e.g., the promoter of the eno1 gene), hxk1 (e.g., the promoter of the hxk1 gene) and pgk1p (e.g., the promoter of the pgk1 gene). In some embodiment, the promoter is adh1p (e.g., the promoter of the adh1 gene). However, is some embodiments, it is preferable to limit the expression of the polypeptide. As such, the promoter controlling the expression of the heterologous polypeptide can be an inducible or modulated promoters such as, for example, a glucose-regulated promoter (e.g., the promoter of the hxt7 gene (referred to as hxt7p)) or a sulfite-regulated promoter (e.g., the promoter of the gpd2 gene (referred to as gpd2p or the promoter of the fzf1 gene (referred to as the fzf1p)), the promoter of the ssu1 gene (referred to as ssu1p), the promoter of the ssu1-r gene (referred to as ssur1-rp). In an embodiment, the promoter is an anaerobic-regulated promoters, such as, for example tdh1p (e.g., the promoter of the tdh1 gene), pau5p (e.g., the promoter of the pau5 gene), hor7p (e.g., the promoter of the hor7 gene), adh1p (e.g., the promoter of the adh1 gene), tdh2p (e.g., the promoter of the tdh2 gene), tdh3p (e.g., the promoter of the tdh3 gene), gpd1p (e.g., the promoter of the gdp1 gene), cdc19p (e.g., the promoter of the cdc19 gene), eno2p (e.g., the promoter of the eno2 gene), pdc1p (e.g., the promoter of the pdc1 gene), hxt3p (e.g., the promoter of the hxt3 gene), dan1 (e.g., the promoter of the dan1 gene) and tpi1p (e.g., the promoter of the tpi1 gene). In an embodiment, the promoter used to allow the expression of the heterologous polypeptide is the adh1p. One or more promoters can be used to allow the expression of each heterologous polypeptides in the recombinant yeast host cell.

One or more promoters can be used to allow the expression of each heterologous polypeptides in the recombinant yeast host cell. In the context of the present disclosure, the expression "functional fragment of a promoter" when used in combination to a promoter refers to a shorter nucleic acid sequence than the native promoter which retain the ability to control the expression of the nucleic acid sequence encoding the heterologous polypeptide. Usually, functional fragments are either 5' and/or 3' truncation of one or more nucleic acid residue from the native promoter nucleic acid sequence.

In some embodiments, the nucleic acid molecules include a one or a combination of terminator sequence(s) to end the translation of the heterologous polypeptide. The terminator can be native or heterologous to the nucleic acid sequence encoding the heterologous polypeptide. In some embodiments, one or more terminators can be used. In some embodiments, the terminator comprises the terminator derived from is from the dit1 gene, from the idp1 gene, from the gpm1 gene, from the pma1 gene, from the tdh3 gene, from the hxt2 gene, from the adh3 gene, from the cyc1 gene, from the pgk1 gene and/or from the ira2 gene. In the context of the present disclosure, the expression "functional variant of a terminator" refers to a nucleic acid sequence that has been substituted in at least one nucleic acid position when compared to the native terminator which retain the ability to end the expression of the nucleic acid sequence coding for the heterologous polypeptide. In the context of the present disclosure, the expression "functional fragment of a terminator" refers to a shorter nucleic acid sequence than the native terminator which retain the ability to end the expression of the nucleic acid sequence coding for the heterologous polypeptide.

The heterologous nucleic acid molecule encoding the one or more heterologous polypeptide, variant or fragment thereof can be integrated in the genome of the yeast host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the yeast host cell's genome. Alternatively, the heterologous nucleic acid molecule can be independently replicating from the yeast's genome. In such embodiment, the nucleic acid molecule can be stable and self-replicating.

The present disclosure also provides nucleic acid molecules for modifying the yeast host cell so as to allow the expression of the one or more heterologous polypeptide, variants or fragments thereof. The nucleic acid molecule may be DNA (such as complementary DNA, synthetic DNA or genomic DNA) or RNA (which includes synthetic RNA) and can be provided in a single stranded (in either the sense or the antisense strand) or a double stranded form. The contemplated nucleic acid molecules can include alterations in the coding regions, non-coding regions, or both. Examples are nucleic acid molecule variants containing alterations which produce silent substitutions, additions, or deletions, but do not alter the properties or activities of the encoded polypeptide, variants or fragments.

In some embodiments, the heterologous nucleic acid molecules which can be introduced into the recombinant host cells are codon-optimized with respect to the intended recipient recombinant yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized heterologous nucleic acid molecule described herein corresponds to between about 0.8 and 1.0, between about 0.8 and 0.9, or about 1.0.

The heterologous nucleic acid molecules can be introduced in the yeast host cell using a vector. A "vector," e.g., a "plasmid", "cosmid" or "artificial chromosome" (such as, for example, a yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The heterologous nucleic acid molecule present in the recombinant host cell can be integrated in the recombinant yeast host cell's genome. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a recombinant yeast host cell are well known in the art and include homologous recombination. The heterologous nucleic acid molecule can be present in one or more copies (e.g., 2, 3, 4, 5, 6, 7, 8 or even more copies) in the recombinant yeast host cell's genome. Alternatively, the heterologous nucleic acid molecule can be independently replicating from the recombinant yeast host cell's genome. In such embodiment, the nucleic acid molecule can be stable and self-replicating.

The present disclosure also provides heterologous nucleic acid molecules that are hybridizable to the complement nucleic acid molecules encoding the heterologous polypeptides as well as variants or fragments. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6X SSC, 0.5% SDS at room temperature for 15 min, then repeated with 2X SSC, 0.5% SDS at 45° C. for 30 min, and then repeated twice with 0.2X SSC, 0.5% SDS at 50° C. for 30 min. For more stringent conditions, washes are performed at higher temperatures in which the washes are identical to those above except for the temperature of the final two 30 min washes in 0.2X SSC, 0.5% SDS are increased to 60° C. Another set of highly stringent conditions uses two final washes in 0.1X SSC, 0.1% SDS at 65° C. An additional set of highly stringent conditions are defined by hybridization at 0.1X SSC, 0.1% SDS, 65° C. and washed with 2X SSC, 0.1% SDS followed by 0.1X SSC, 0.1% SDS.

Hybridization requires that the two nucleic acid molecules contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived. For hybridizations with shorter nucleic acids, i.e., oligonucleotides, the position of mismatches becomes more important, and the length of the oligonucleotide determines its specificity. In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

In some embodiments of the present disclosure, the heterologous polypeptides having 1,4-β-glucosidase activity can have the amino acid sequence of SEQ ID NO: 1, 2, 3, 4, or 5 or be encoded by a nucleic acid sequence encoding the amino acid sequence of SEQ ID NO: 1, 2, 3, 4, or 5. In some embodiments, the heterologous polypeptides include variants of the 1,4-β-glucosidase polypeptides of SEQ ID NO: 1, 2, 3, 4, or 5 (also referred to herein as 1,4-β-glucosidase variants). A variant comprises at least one amino acid difference (substitution or addition) when compared to the amino acid sequence of the 1,4-β-glucosidase polypeptide of SEQ ID NO: 1, 2, 3, 4, or 5. The 1,4-β-glucosidase variants do exhibit 1,4-β-glucosidase activity. In an embodiment, the variant 1,4-β-glucosidase exhibits at least 50%, 60%, 70%, 80%, 90%, 95%, 96%, 97%, 98% or 99% of the 1,4-β-glucosidase activity of the corresponding wild-type polypeptides having the amino acid sequence of SEQ ID NO: 1, 2, 3, 4, or 5. The 1,4-β-glucosidase variants also have at least 70%, 80%, 85%, 90%, 95%, 96%, 97%, 98% or 99% identity to the corresponding wild-type polypeptides having the amino acid sequence of SEQ ID NO: 1, 2, 3, 4, or 5. The term "percent identity", as known in the art, is a relationship between two or more polypeptide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant 1,4-β-glucosidase described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions are known in the art and are included herein. Non-conservative substitutions, such as replacing a basic amino acid with a hydrophobic one, are also well-known in the art.

A variant 1,4-β-glucosidase can also be a conservative variant or an allelic variant. As used herein, a conservative variant refers to alterations in the amino acid sequence that do not adversely affect the biological functions of the 1,4-β-glucosidase. A substitution, insertion or deletion is said to adversely affect the polypeptide when the altered sequence prevents or disrupts a biological function associated with the 1,4-β-glucosidase (e.g., the hydrolysis of starch into glucose). For example, the overall charge, structure or hydrophobic-hydrophilic properties of the polypeptide can be altered without adversely affecting a biological activity. Accordingly, the amino acid sequence can be altered, for example to render the peptide more hydrophobic or hydrophilic, without adversely affecting the biological activities of the 1,4-β-glucosidase.

In some embodiments of the present disclosure, the heterologous polypeptides can be fragments of the amino acid sequence of SEQ ID NO: 1, 2, 3, 4, or 5 or fragments from the variants described herein. A fragment comprises at least one less amino acid residue when compared to the amino acid sequence of the 1,4-β-glucosidase polypeptide or variant and still possess the enzymatic activity of the full-length 1,4-β-glucosidase. In an embodiment, the 1,4-β-glucosidase fragment exhibits at least 50%, 60%, 70%, 80%, 90%, 95%, 96%, 97%, 98% or 99% of the activity of the corresponding wild-type polypeptides having the amino acid of SEQ ID NO: 1, 2, 3, 4, or 5. The 1,4-β-glucosidase fragments can also have at least 70%, 80%, 85%, 90%, 95%, 96%, 97%, 98% or 99% identity when compared to the corresponding wild-types polypeptides having the amino acid sequence of SEQ ID NO: 1, 2, 3, 4, or 5. The fragment can be, for example, a truncation of one or more amino acid residues at the amino-terminus, the carboxy terminus or both termini of the 1,4-β-glucosidase polypeptide or variant. Alternatively or in combination, the fragment can be generated from removing one or more internal amino acid residues. In an embodiment, the 1,4-β-glucosidase fragment has at least 100, 150, 200, 250, 300, 350, 400, 450, 500 or more consecutive amino acids of the 1,4-β-glucosidase polypeptide or the variant.

In some embodiments, a fragment refers to the amino acid sequence of SEQ ID NO: 1, 2, 3, 4, or 5 to which the signal sequence has been removed. For example, the heterologous polypeptide can have the amino acid sequence corresponding to positions between 20 and 860 of SEQ ID NO: 1 which specifically exclude the native signal sequence (located between positions 1 and 19 of SEQ ID NO: 1). In another example, the heterologous polypeptide can have the amino acid sequence corresponding to positions between 18 to 876 of SEQ ID NO: 3 (which specifically exclude the native signal sequence (located between positions 1 and 17 of SEQ ID NO: 3).

In the context of the present disclosure, the polypeptides having 1,4-β-glucosidase activity can be derived from any organisms, but may be, in some embodiments, from yeast or fungus, for example, from the genus *Aspergillus, Saccharomycopsis,* or *Brettanomyces*. In an embodiment, the polyptides having 1,4-β-glucosidase activity may be derived from *Aspergillus niger, Aspergillus oryzae, Saccharomycopsis fibuligera, Brettanomyces anonmalus,* or *Brettanomyces bruxellensis.*

In some instances, the polypeptides having 1,4-β-glucosidase activity can be derived from a fungus from the genus *Aspergillus*. In an embodiment, the polypeptides having 1,4-β-glucosidase activity can be derived from a fungus from the species *Aspergillus niger*, and include 1,4-β-glucosidases comprising the amino acid sequence of SEQ ID NO: 1, a variant of SEQ ID NO: 1, or a fragment of SEQ ID NO: 1. In an embodiment, the polypeptides having 1,4-β-glucosidase activity can be derived from a fungus from the species *Aspergillus oryzae*, and include 1,4-β-glucosidases comprising the amino acid sequence of SEQ ID NO: 2, a variant of SEQ ID NO: 2, or a fragment of SEQ ID NO: 2.

In some instances, the polypeptides having 1,4-β-glucosidase activity can be derived from a yeast from the genus *Saccharomycopsis*. In an embodiment, the polypeptides having 1,4-β-glucosidase activity can be derived from a fungus from the species *Saccharomycopsis fibuligera*, and include 1,4-β-glucosidases comprising the amino acid sequence of SEQ ID NO: 3, a variant of SEQ ID NO: 3, or a fragment of SEQ ID NO: 3.

In some instances, the polypeptides having 1,4-β-glucosidase activity can be derived from a yeast from the genus *Brettanomyces*. In an embodiment, the polypeptides having 1,4-β-glucosidase activity can be derived from a yeast from the species *Brettanomyces anonmalus*, and include 1,4-β-glucosidases comprising the amino acid sequence of SEQ ID NO: 4, a variant of SEQ ID NO: 4, or a fragment of SEQ ID NO: 4. In an embodiment, the polypeptides having 1,4-β-glucosidase activity can be derived from a yeast from the species *Brettanomyces bruxellensis*, and include 1,4-β-glucosidases comprising the amino acid sequence of SEQ ID NO: 5, a variant of SEQ ID NO: 5, or a fragment of SEQ ID NO: 5.

In some embodiments, the polypeptide having 1,4-β-glucosidase activity is a polypeptide of formula (II) or (III):

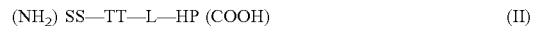

$$(NH_2)\ SS\text{---}TT\text{---}L\text{---}HP\ (COOH) \quad\quad (II)$$

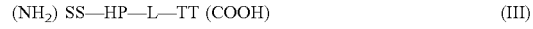

$$(NH_2)\ SS\text{---}HP\text{---}L\text{---}TT\ (COOH) \quad\quad (III)$$

wherein:
HP is the heterologous polypeptide having 1,4-β-glucosidase activity;
L is present or absent and is an amino acid linker;
TT is present or absent and is an amino acid tethering moiety for associating the polypeptide to a cell wall or cell membrane of the recombinant yeast host cell;
SS is present or absent and is a signal sequence moiety;
(NH$_2$) indicates the amino terminus of the polypeptide;
(COOH) indicates the carboxyl terminus of the polypeptide; and
"-" is an amide linkage.

In other embodiments, the polypeptides of the present disclosure can be secreted. When the polypeptides are secreted, they are transported to outside of the cell. In such embodiments, the heterologous polypeptides having 1,4-β-glucosidase activity of formula (I) and (II) have a SS moiety but lack a TT moiety.

In some embodiments, the polypeptides of the present disclosure remain physically associated with the recombinant yeast host cell when secreted. In an embodiment, at least one portion (usually at least one terminus) of the polypeptide is bound, covalently, non-covalently and/or electrostatically for example, to cell wall (and in some embodiments to the cytoplasmic membrane). For example, the polypeptide can be modified to bear one or more transmembrane domains, to have one or more lipid modifications (myristoylation, palmitoylation, farnesylation and/or prenylation), to interact with one or more membrane-associated polypeptide and/or to interactions with the cellular lipid rafts. While the polypeptide may not be directly bound to the cell membrane or cell wall (e.g., such as when binding occurs via a tethering moiety), due to the polypeptide's physical association with the cell, it is nonetheless considered a "cell-associated" polypeptide according to the present disclosure. In some embodiments, the polypeptides, when expressed, include one or more signal sequences for facilitating the secretion of the polypeptides. The signal sequences may be cleaved during the secretion of the polypeptides to an extracellular space.

In some embodiments, the heterologous polypeptide of the present disclosure is "cell-associated" to the recombinant yeast host cell because it is designed to be expressed and remain physically associated with the recombinant yeast host cells. In an embodiment, the polypeptide can be expressed inside the recombinant yeast host cell (intracellularly). In such embodiment, the polypeptide does not need to be associated to the recombinant yeast host cell's wall. When the polypeptide is intended to be expressed intracellularly, its signal sequence, if present in the native sequence, can be deleted to allow intracellular expression.

In some embodiments, the heterologous polypeptide can be expressed to be located at and associated to the cell wall of the recombinant yeast host cell. In some embodiments, the polypeptide is expressed to be located at and associated to the external surface of the cell wall of the host cell. Recombinant yeast host cells all have a cell wall (which includes a cytoplasmic membrane) defining the intracellular (e.g., internally-facing the nucleus) and extracellular (e.g., externally-facing) environments. The polypeptide can be located at (and in some embodiments, physically associated to) the external face of the recombinant yeast host's cell wall and, in further embodiments, to the external face of the recombinant yeast host's cytoplasmic membrane. In the context of the present disclosure, the expression "associated to the external face of the cell wall/cytoplasmic membrane of the recombinant yeast host cell" refers to the ability of the polypeptide to physically integrate (in a covalent or non-covalent fashion), at least in part, in the cell wall (and in some embodiments in the cytoplasmic membrane) of the recombinant yeast host cell. The physical integration can be attributed to the presence of, for example, a transmembrane domain on the polypeptide, a domain capable of interacting with a cytoplasmic membrane protein on the polypeptide, a post-translational modification made to the polypeptide (e.g., lipidation), etc. In some embodiments, the polypeptides having 1,4-β-glucosidase activity which are associated to the membrane of the recombinant yeast host cell of formula (I) or (II) have a SS moiety and a TT moiety, with an optional L moiety.

In some embodiments, the heterologous polypeptides of the present disclosure can be expressed inside the recombinant yeast host cell, e.g., intracellularly. In such embodiments, the polypeptides having 1,4-β-glucosidase activity of formula (I) or (II) lack the SS moiety, the L moiety and the TT moiety. The polypeptides of the present disclosure expressed intracellularly can be modified to remove, if any, signal peptide sequences present in the native amino acid sequence of the polypeptide to allow for an intracellular expression.

Recombinant Yeast Host Cell

The recombinant yeast host cells of the present disclosure are intended for use in a fermentation process for making an alcoholic and fermented beverage intended for human consumption. In an embodiment, the recombinant yeast host cells can be used, for example, in a fermentation process for making alcoholic beverages, such as beer (including but not limited to ale and/or lager), and wine.

The recombinant yeast host cells of the present disclosure can be provided in an active form (e.g., liquid (such as, for example, a cream yeast), compressed, or fluid-bed dried yeast), in a semi-active form (e.g., liquid, compressed, or fluid-bed dried), in an inactive form (e.g., drum- or spray-dried) as well as a mixture thereof. In an embodiment, the recombinant yeast host cells are provided in an active and dried form. In some embodiments, the recombinant yeast host cell can be provided in a composition with an emulsifier.

The present disclosure concerns recombinant yeast host cells that have been genetically engineered. The recombinant yeast host cells have a heterologous nucleic acid molecule encoding one or more heterologous polypeptide having 1,4-β-glucosidase activity ("β-glucosidase") for hydrolyzing the β-glycosidic linkages of non-volatile conjugates, which bond a volatile flavor compound to a sugar molecule.

In some embodiments, the recombinant yeast host cells can include further additional genetic modifications. In some embodiments, the recombinant yeast host cell can include further heterologous nucleic acid molecules encoding one or more further heterologous polypeptide. Alternatively or in combination, the recombinant yeast host cell can include a genetic modification to delete or inactivate one or more of a native gene.

In one embodiment, the recombinant yeast host cell can include one or more further heterologous nucleic acid molecule encoding for a heterologous polypeptide having acetolactate decarboxylase (ALDC) activity, a variant thereof having ALDC activity, or a fragment thereof having ALDC activity. Recombinant yeast host cells capable of expressing polypeptides having ALDC activity can be used, for example, for reducing the off-flavors of an alcoholic beverage such as beer (for example by reducing diacetyl in an alcoholic beverage such as beer). Embodiments of recombinant yeast host cell comprising a heterologous nucleic acid molecule encoding for a heterologous polypeptide having ALDC activity and capable of expressing the heterologous polypeptide having ALDC activity have been described in WO2020/058914, which is incorporated herewith in its entirety.

In another embodiment, the recombinant yeast host cell can include one or more genetic modification for the production of a flavor compound (which may or may not be volatile). In such embodiments, the recombinant yeast host cell can include one or more further heterologous nucleic acid molecules encoding a heterologous polypeptide involved in the production of the flavor compound. In some additional embodiments, the recombinant yeast host cell can include one or more genetic modification to delete or inactivate a native gene involved in the production of the flavor compound. The flavor compound can be, for example, lactic acid, valencene, nootkatone, vanillin, isoamyl acetate 4-(4-hydroxyphenyl)-2-butanone, 4-ethyl-phenol, 4-ethyl guiacol, phenylethyl alcohol, ethyl capraote, vanillyloctanamide as well as combinations thereof. Embodiments of recombinant yeast host cell comprising one or more genetic modifications to allow or enhance the production of a flavor compound have been described in WO2019/171230, which is incorporated herewith in its entirety.

In the context of the present disclosure, when a recombinant yeast cell is qualified as being "genetically engineered", it is understood to mean that it has been manipulated to add at least one or more heterologous or exogenous nucleic acid residue. In some embodiments, the one or more nucleic acid residues that are added can be derived from a heterologous cell or the recombinant host cell itself. In the latter scenario, the nucleic acid residue(s) is (are) added at one or more genomic location which is different than the native genomic location. The genetic manipulations did not occur in nature and are the results of in vitro manipulations of the yeast.

The present disclosure concerns recombinant yeast host cells that have been genetically engineered. The genetic modification(s) is(are) aimed at increasing the expression of a specific targeted gene (which is considered heterologous to the yeast host cell) and can be made in one or multiple (e.g., 1, 2, 3, 4, 5, 6, 7, 8 or more) genetic locations. In some embodiments, the one or more nucleic acid residues that are added can be derived from a heterologous cell or the recombinant yeast host cell itself. In the latter scenario, the nucleic acid residue(s) is (are) added at one or more genomic location which is different than the native genomic location. The genetic manipulations did not occur in nature and are the results of in vitro manipulations of the yeast. The genetic modification(s) in the recombinant yeast host cell of the present disclosure comprise, consist essentially of or consist of a genetic modification allowing the expression of a heterologous nucleic acid molecule encoding a heterologous polypeptide having 1,4-β-glucosidase activity. In the context of the present disclosure, the expression "a genetic modification allowing the expression of a heterologous nucleic acid molecule encoding a heterologous polypeptide having 1,4-β-glucosidase activity" refers to the fact that the recombinant yeast host cell can include other genetic modifications which are unrelated to the anabolism or the catabolism of the non-volatile conjugates or ethanol.

In the context of the present disclosure, the recombinant host cell is a yeast and in some embodiments the yeast can be used in the production of alcoholic beverages. Suitable recombinant yeast host cells can be, for example, from the genus *Saccharomyces, Kluyveromyces, Arxula, Debaryomyces, Candida, Pichia, Phaffia, Schizosaccharomyces, Hansenula, Kloeckera, Schwanniomyces, Torula, Hanseniaspora, Lachancea, Wickerhamomyces* or *Yarrowia*. Suitable yeast species can include, for example, *S. cerevisiae, S. bulderi, S. barnetti, S. exiguus, S. uvarum, S. diastaticus, C. utilis, K. lactis, K. marxianus K. fragilis, Hanseniaspora vineae, Lachancea fermentati, Lachancea thermotolerans, Schizosaccharomyces japonicus* and/or *Wickerhamomyces anomalus*. In some embodiments, the yeast is selected from the group consisting of *Saccharomyces cerevisiae, Schizosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In some embodiment, the host cell can be an oleaginous yeast cell. For example, the oleaginous yeast host cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiment, the host cell can be an oleaginous microalgae host cell (e.g., for example, from the genus *Thraustochytrium* or *Schizochytrium*). In an embodiment, the recombinant yeast host cell is from the genus *Saccharomyces* and, in some embodiments, from the species *Saccharomyces cerevisiae*. In an embodiment, the recombinant yeast host cell is from the genus *Saccharomyces* sp. and in some embodiments from the species *Saccharomyces pastorianus*. In some embodiments, the recombinant yeast host cell is an interspecies hybrid between *Saccharomyces cerevisiae* and *Saccharomyces eubayanus*.

Because the recombinant yeast host cell is intended to be used for the production of a fermented alcoholic beverage, in some embodiments, it must be able to generate the appropriate congener profile for such fermented alcoholic beverage. As it is known in the art, congeners are substances, different from ethanol, that are produced during fermentation and are associated with an organoleptic profile specific for the fermented alcoholic beverage. As such, when the recombinant yeast host cell is obtained from a brewing (beer) strain, it is expected, in some embodiments, to be able to generate a substantially similar congener profile of such brewing (beer) strain and generate additional flavors associated with the hydrolysis of the non-volatile conjugates or non-volatile flavor compound precursors. In another example, when the recombinant yeast host cell is obtained from a wine strain, it is expected, in some embodiments, to be able to generate a substantially similar congener profile of such wine strain and generate additional flavors associated with the hydrolysis of the non-volatile conjugates or non-volatile flavor compound precursors. In yet another example, when the recombinant yeast host cell is obtained from a distilled spirit strain, it is expected, in some embodiments, to be able to generate a substantially similar congener profile of such distilled spirit strain and generate additional flavors associated with the hydrolysis of the non-volatile conjugate or non-volatile flavor compound precursors. It is known in the art that biofuel strains are not capable of generating the appropriate congener profile for making a fermented alcoholic beverage and, in some embodiments, cannot be used to obtain the recombinant yeast host cell of the present disclosure.

In some embodiments, the recombinant *Saccharomyces cerevisiae* can be obtained from a brewing strain of *Saccharomyces cerevisiae*. For example, the recombinant *Saccharomyces* sp. can be obtained from a strain of *Saccharomyces* sp. capable of metabolizing a medium comprising, as a majority of carbohydrates (in weight percentage), maltose and maltotriose. In the context of the present disclosure, a brewing strain refers to a yeast strain capable of producing an alcoholic beer, including the ethanol content and the congener profile usually found in beer. Brewing strains include, without limitations, ale strains (such as, for example, a *Saccharomyces cerevisiae* strain) and lager strains (such as, for example, a *Saccharomyces pastorianus* strain). In some embodiments, the brewing strain can be obtained from a strain of *Saccharomyces* sp. which usually reproduce using asexual reproduction or budding (for example a non-sporulating *Saccharomyces* sp. strain). Alternatively, the brewing strain can be obtained from a strain of *Saccharomyces* sp. which only reproduces using asexual reproduction or budding (for example a non-sporulating *Saccharomyces* sp. strain). In another embodiment, the brewing strain is capable of metabolizing a fermenting medium comprising, as the majority of the carbohydrates, maltose and maltotriose. In still another embodiment, the brewing strain is obtained from a *Saccharomyces* sp. strain which usually fails to produce a killer protein. Alternatively, the brewing strain is obtained from a *Saccharomyces* sp. strain which fails to produce a killer protein. In yet another embodiment, the brewing strain is obtained from a *Saccharomyces* sp. strain which has a low tolerance towards alcohol. In some embodiments the brewing strain is obtained from a *Saccharomyces* sp. strain which has tolerance towards up to 15%, up to 14%, up to 13%, up to 12%, up to 11%, or up to 10% v/v alcohol.

In some embodiments, the recombinant *Saccharomyces cerevisiae* can be obtained from a wine strain of *Saccharomyces cerevisiae*. For example, the recombinant *Saccharomyces* sp. can be obtained from strain of *Saccharomyces* sp. capable of metabolizing a medium comprising glucose, fructose and sucrose.

In the context of the present disclosure, a wine strain refers to a yeast strain capable of producing an alcoholic wine, including the ethanol content and the congener profile usually found in wine. Wine strains include, without limitations, *Saccharomyces* sp. (such as, for example, *Saccharomyces cerevisiae*); *Torulaspora* sp. (such as, for example, *Torulaspora delbrueckii*); *Lachancea* sp. (such as, for example, *Lachancea thermotolerans*); *Metschnikowia* sp. (such as, for example, *Metschnikowia pulcherrima*); *Schizosaccharomyces* sp. (such as, for example, *Schizosaccharomyces pombe*); *Pichia* sp. (such as, for example, *Pichia guillermondii* or *Pichia kluyven*); *Hansenula* sp. (such as, for example, *Hansenula anomala*) and *Starmerella* sp. (such as, for example, *Starmerella bacillaris*). In some embodiments, the wine strain can be obtained from a strain of *Saccharomyces* sp. which usually reproduces using sexual reproduction (for example a sporulating *Saccharomyces* sp. strain). Alternatively, the wine strain can be obtained from a strain of *Saccharomyces* sp. which only reproduces using sexual reproduction (for example a sporulating *Saccharomyces* sp. strain). In another embodiment, the wine strain is capable of metabolizing a fermenting a medium comprising glucose, fructose and sucrose. In still another embodiment, the wine strain is obtained from a *Saccharomyces* sp. strain which usually produces a killer protein. Alternatively, the wine strain is obtained from a *Saccharomyces* sp. strain which produces a killer protein.

In the context of the present disclosure, a brewing strain refers to a yeast strain capable of producing an alcoholic beer, including the ethanol content and the congener profile usually found in beer. In some embodiments, the brewing strain can be obtained from a strain of *Saccharomyces* sp. which usually reproduce using asexual reproduction or budding (for example a non-sporulating *Saccharomyces* sp. strain). Alternatively, the brewing strain can be obtained from a strain of *Saccharomyces* sp. which only reproduces using asexual reproduction or budding (for example a non-sporulating *Saccharomyces* sp. strain). In another embodiment, the brewing strain is capable of metabolizing a fermenting a medium comprising maltose and maltotriose. In still another embodiment, the brewing strain is obtained from a *Saccharomyces* sp. strain which usually fails to produce a killer protein. Alternatively, the wine strain is obtained from a *Saccharomyces* sp. strain which fails to produce a killer protein.

In some embodiments, the recombinant yeast host cells are wine and brewing strains. As used herein, "wine strains" and "brewing strains" refer to yeast strains which have been selected for their ability to create flavor profiles associated with wine and beer, respectively, after fermenting.

In some embodiments, both wine and brewing yeast are *Saccharomyces cerevisiae*. *S. cerevisiae* has been referred as "brewing yeast" because it was originally discovered in a brewery, but yeast has since been evolved and domesticated for wine making. There are hundreds of commercial strains available for making wine or beer. There are at least three key differences or attributes between brewing yeast and wine yeast. First, wine yeasts typically ferment glucose and fructose sugars provided by grapes. They do not efficiently metabolize maltose and often are incapable of utilizing maltotriose. Genetically, these strains have often lost copy numbers or complete genes associated with maltose/maltotriose utilization. Brewing yeasts are very efficient in metabolizing both maltose and maltotriose. Secondly, wine yeasts are typically killer yeast, in which they produce a killer toxin capable of killing other *Saccharomyces* and wild yeasts. This is often a preferred trait for wine makers in which the process is less sterile and often harbors many wild microbes from the grapes. Brewing yeasts are typically not killer strains. Thirdly, wine yeasts are far less domesticated than brewing yeasts and are often still capable of sporulating and undergoing sexual reproduction. Brewing yeasts are sufficiently domesticated that most have lost the genes or ability to sporulate and rely solely on asexual reproduction, or budding. As such, a skilled person is capable of distinguishing appropriate yeast strains that have been selected for making beer or wine as well as the flavor profile associated with these beverages.

In contrast, a biofuel yeast strain may be a yeast strain having high alcohol tolerance (e.g., above 15-20% w/v) and having the ability to utilize and ferment, primarily monomeric sugars, in a rapid manner. The primary sugar in biofuel production, particularly corn ethanol, is glucose where starch is hydrolyzed into smaller dextrins via α-amylase and subsequently converted to glucose via glucoamylase. Because glucoamylase can efficiently hydrolyze maltotriose into glucose, many biofuel strains have lost the ability to utilize this trisaccharide. In particular, the loss of the AGT1 gene, which has a high affinity to maltose/maltotriose transporter, is common among biofuel strains. Utilization of DP2/DP3 sugars requires a great deal of energy for yeast, so it is not surprising that yeasts that have been domesticated for rapid growth and fermentation have found ways to conserve this energy, particularly in environments where low concentrations of complex sugars exist. In some embodiments, the recombinant yeast host cell of the present disclosure is not a biofuel strain and is not obtained from genetically modifying a biofuel strain.

In some embodiments, the recombinant yeast host cells provided herein express a maltotriose transporter. In one embodiment, the recombinant yeast host cells express native maltotriose transporter. In one embodiment, the recombinant yeast host cells express recombinant maltotriose transporter. In one embodiment, the maltotriose transporter is AGT1, a variant thereof or a fragment thereof.

The present disclosure concerns recombinant yeast host cells having the intrinsic ability to make a minimal amount of ethanol suitable in the manufacture of an alcoholic beverage by fermentation. For example, the recombinant yeast host cells can express one or more polypeptide (which can be endogenous/native or heterologous) in an ethanol production pathway in order to achieve a minimal amount of ethanol during or after the fermentation. In some embodiments, the minimal amount of ethanol is at least 5 g/L, 10 g/L, 20 g/L, 30 g/L, 40 g/L, 50 g/L or more during or after fermentation (but prior to distillation, if any), or after at least partial conversion of the carbohydrate substrate into its metabolites. In one embodiment, the minimal amount of ethanol produced by the recombinant yeast host cell is 5 g/L. The recombinant yeast host cell of the present disclosure may have a native (e.g., not genetically modified) and functional ethanol production pathway to allow it to reach the minimal ethanol level during fermentation. Enzymes involved in ethanol production include, but are not limited to, pyruvate decarboxylase (PDC), alcohol dehydrogenase (ALD), lactate dehydrogenase (LDH), glucokinase, glucose-6-phosphate isomerase, phosphofructokinase, aldolase, triosephosphate isomerase, glyceraldehyde 3-phosphate dehydrogenase, 3-phosphoglycerate kinase, phosphoglycerate mutase, enolase, pyruvate kinase, pyruvate decarboxylase and/or alcohol dehydrogenase.

Process for Making an Alcoholic Beverage

The recombinant yeast host cell of the present disclosure has been designed to be used in the preparation of a fermented beverage beverages for human consumption from a fermentable medium comprising fermentable carbohydrates and non-volatile conjugates. The present disclosure thus provides a process comprising contacting the recombinant yeast host cell or composition described herein with the fermentable medium under conditions to allow the hydrolysis of the β-glycosidic linkages of non-volatile conjugates and the generation of an alcohol (e.g., fermenting step).

In an embodiment, the process of the present disclosure is conducted at a temperature equal to or below about 28° C. (at 27, 26, 25, 24, 23, 22, 21, 20, 19, 18, 17, 16, 15, 14, 13, 12, 11, 10, 9, 8, 7, 6, 5, 4 or 3° C.). In some embodiments, the fermentable medium is fermented at a temperature between about 3 to about 28° C. In some specific embodiments, the fermentable medium is fermented at a temperature of equal to or above about 3, 4, 5, 6, 7, 8, 9, 10, 11, 12, 13, 14, 15, 16, 17, 18, 19, 20, 21, 22, 23, 24, 25, 26 or 27° C. In another specific embodiment, the fermentable medium is fermented at a temperature of equal to or below about 28, 27, 26, 25, 24, 23, 22, 21, 20, 19, 18, 17, 16, 15, 14, 13, 12, 11, 10, 9, 8, 7, 6, 5 or 4° C. In still another specific embodiment, the fermentable medium is fermented at a temperature between about 3, 4, 5, 6, 7, 8, 9, 10, 11, 12, 13, 14, 15, 16, 17, 18, 19, 20, 21, 22, 23, 24, 25, 26 or 27° C. and about 28, 27, 26, 25, 24, 23, 22, 21, 20, 19, 18, 17, 16, 15, 14, 13, 12, 11, 10, 9, 8, 7, 6, 5 or 4° C.

In an embodiment, especially when an ale beer is being produced, the fermentable medium is fermented at a temperature between about 15 to about 24° C. In some specific embodiments, the fermentable medium is fermented at a temperature of equal to or above about 15, 16, 17, 18, 19, 20, 21, 22 or 23° C. In another specific embodiment, the fermentable medium is fermented at a temperature of equal to or below about 24, 23, 22, 21, 20, 19, 18, 17 or 16° C. In still another specific embodiment, the fermentable medium is fermented at a temperature between about 15, 16, 17, 18, 19, 20, 21, 22 or 23° C. and about 24, 23, 22, 21, 20, 19, 18, 17 or 16° C.

In an embodiment, especially when a lager beer is being produced, the fermentable medium is fermented at a temperature between about 3 to about 15° C. In some specific embodiments, the fermentable medium is fermented at a temperature of equal to or above about 3, 4, 5, 6, 7, 8, 9, 10, 11, 12, 13 or 14° C. In another specific embodiment, the fermentable medium is fermented at a temperature of equal to or below about 15, 14, 13, 12, 11, 10, 9, 8, 7, 6, 5 or 4° C. In still another specific embodiment, the fermentable medium is fermented at a temperature between about 3, 4, 5, 6, 7, 8, 9, 10, 11, 12, 13 or 14° C. and about 15, 14, 13, 12, 11, 10, 9, 8, 7, 6, 5 or 4° C.

In some embodiments, it may be advantageous to provide the recombinant yeast host cell of the present disclosure as a fermentation agent. The fermentation agent can include 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or more of the recombinant yeast host cell of the present disclosure. In one embodiment, a fermentation agent for making a fermented alcoholic beverage comprising, consisting essentially or consisting of the recombinant yeast host cell described herein. As used herein, "consisting essentially of" or "consist of" in reference to a fermentation agent refers to a population of fermenting organisms which do not include a substantial amount of additional fermenting or flavoring organisms which participate to the fermentation process. In an embodiment, a fermentation agent consisting essentially of the recombinant yeast host cell of the present disclosure is made up of at least 50%, 60%, 70%, 80%, 85%, 90%, 95%, 99%, or 99.9% of the recombinant yeast host cell described herein. In still another embodiment, a fermentation agent consisting essentially of the recombinant yeast host cell of the present disclosure is a monoculture of one strain of a recombinant yeast host cell. Alternatively, a fermentation agent comprising of the recombinant yeast host cell of the present disclosure is a combination of more than one strains of the recombinant yeast host cell described herein or a combination of the recombinant yeast host cell described herein and one or more of a non-genetically modified yeast host cell.

As used herein, "fermentable carbohydrates" includes biomass that can be fermented with the recombinant host cell described herein to make a fermented alcoholic beverage includes any type of biomass known in the art and described herein. For example, the biomass can include, but is not limited to, starch and/or sugar. Starch materials can include, but are not limited to, mashes such as corn, wheat, rye, barley, rice, or milo. Sugar materials can include, but are not limited to, grapes. Alternatively, the biomass can include, but not limited, a wort. Wort is a liquid extracted from the mashing process during the brewing of beer or whisky. Wort typically contains sugars, such as maltose and/or maltotriose, that will be fermented by the brewing yeast to produce alcohol as well as small amounts of non-fermentable larger dextrins. Wort typically also contains amino acids to provide nitrogen to the yeast as well as more complex proteins contributing to beer head retention and flavor. Wort can be made from materials, such as mashes of corn, wheat, rye, barley, rice, or milo. In some embodiments, the biomass comprises grape components, such as, for example, a grape must.

In some embodiments, the fermentable medium comprises the non-volatile conjugates prior to the addition of the recombinant yeast host or composition to the fermentable medium. In other embodiments, fermentable medium is supplemented with the non-volatile conjugate at the same time or after the addition of the recombinant yeast host cell or composition to the fermentable medium. In one embodiments, the fermentable medium comprises the non-volatile conjugate prior to the addition of the recombinant yeast host or composition, and is also supplemented with the non-volatile conjugate at the same time or after the addition of the recombinant yeast host cell or composition to the fermentable medium.

In the process described herein, hydrolysis of the β-glycosidic linkages of non-volatile conjugates, which bond volatile flavor compounds to sugar molecules, occurs during and/or after fermentation (e.g., the production of ethanol). In one embodiment, hydrolysis of the β-glycosidic linkages occurs during fermentation. In one embodiment, hydrolysis of the β-glycosidic linkages occur after fermentation. In one embodiment, hydrolysis of β-glycosidic linkages occur during and after fermentation. As used herein, "fermentation" refers to the conversion of at least some of the fermentable carbohydrates into ethanol by the recombinant yeast host cell. For example, fermentation refers to conversion of at least 10%, at least 20%, at least 30%, at least 40%, at least 50%, at least 60%, at least 70%, at least 80%, or at least 90% of the fermentable carbohydrates into ethanol by the recombinant yeast host cell.

In some embodiments, the fermentable medium is supplemented with a hop before, during, and/or after fermentation of the fermentable medium. A hop is the flower of a hop plant (such as *Humulus lupulus*). In some embodiments, the fermentable medium is supplemented with a hop before fermentation. In some embodiments, the fermentable medium is supplemented with a hop during fermentation. In some embodiments, the fermentable medium is supplemented with a hop after fermentation. In some embodiments, the fermentable medium is supplemented with a hop before and during fermentation. In some embodiments, the fermentable medium is supplemented with a hop during and after fermentation. In some embodiments, the fermentable medium is supplemented with a hop before, during, and after fermentation. It is well known in the art that the amount of hop being added to a fermentable medium is going to depend on the desired flavor/odor profile, hop variety, the season at which the hop has been harvested and/or the amount of time the hop has been stored prior to use. As such, it is within the skills of the person skilled in the art to determine how much hop can or should be added to the fermentation medium.

In some embodiments, the fermentable medium is boiled together with the hop. Alternatively or in combination, the fermentable medium is supplemented with a hop after boiling. It is well known in the art that the conditions for boiling the fermentable medium (in the presence of absence of hop) are going to depend on the desired flavor/odor profile and/or the style of beverage (such as the style of beers). As such, it is within the skills of the person skilled in the art to determine the conditions for boiling the fermentable medium.

In some embodiments, the volatile flavor compound (VFC) is a terpenoid. In one embodiment, the volatile flavor compound (VFC) is a monoterpene alcohol. In some embodiments, the non-volatile conjugate is a terpene glycoside. In some embodiments, the non-volatile conjugate is derived from a hop.

In the context of the present disclosure, the process described herein is in certain embodiments for making beer. In some embodiments, the fermentable carbohydrates of the fermentable medium comprise a majority, in weight, of maltose and/or maltotriose. In one embodiment, the fermentable medium comprises maltose. In one embodiment, the fermentable medium comprises maltotriose. In one embodiment, the fermentable medium comprises maltose and maltotriose. In some embodiments, the fermentable medium comprises about 30%, 40%, 50%, 60%, or 70% maltose. In one embodiment, the fermentable medium comprises about 50% maltose. In some embodiments, the fermentable medium comprises 5%, 10%, 12%, 14%, 16%, 18%, 20%, 22%, 25%, or 30% maltotriose. In one embodiment, the fermentable medium comprises about 18% maltotriose.

In an embodiment, the recombinant yeast host cell of the present disclosure can be used in a brewing process to make a beer (such as, for example, an ale or a lager beer). Process for making beer include, without limitation, contacting the recombinant yeast host cell (alone or in a combination) of the present disclosure with a wort as a carbohydrate substrate to provide maltose and maltotriose and ferment the wort until at least 5 g/L of ethanol is obtained and, at least some of the non-volatile conjugate or non-volatile flavor compound precursor is hydrolyzed.

Brewing typically contains four main ingredients: water, cereal, hops, and yeast. The brewing process begins with milling the partially germinated and dried grains (referred to as malted cereals), with the most common grain being barley. The malt is cracked during the milling process to break up the grain kernels and expose the starch molecules. The milled grains are transferred to a mash tun where it is mixed with warm water, typically between 37-76° C., activating the natural amylolytic enzymes (for example 60 to 69° C. for amylases and/or 38 to 49° C. for proteases) which begin to degrade the starches creating fermentable sugars, primarily maltose and maltotriose. Optionally, exogenous enzyme can be added to further enhance sugar conversion and reduce viscosity. After approximately one to two hours, the mash is pumped to the lauter tun where the sugar water (now referred to as a wort), is separated from the spent grain. First, a mashout is typically performed in which the mash temperature is raised to >77° C. to inactivate the enzymes and preserve the sugar profile. The wort is then drained from the bottom as the lauter tun typically has a perforated or false bottom which allows the wort to filter through, leaving behind the solids. The wort is initially recirculated to the top of the lauter tun to allow the grains to compress and act as a natural filter. Once the wort begins to run clear with less grain particulates, the wort is transferred to the boil kettle. The grain bed is then sparged, the process of rinsing the grains with hot water to wash and extract as much of the sugar as possible.

The sparge is collected with the initial wort runoffs into the kettle which is boiled to both sterilize the wort, but also for hop additions to impart the aromatic and bitter qualities of the beer. The boiling can be performed to isomerize the hop's alpha acids, solubilizing them and enhancing the bitter taste. The earlier the hops are added in the boil, the more isomerization and bittering effect. Therefore, the hop schedule can be carefully designed for each recipe to balance the bitter and aromatic contributions of each hop species, with early boil additions targeting bitterness, mid-boil addition targeting both flavor and aroma, and late boil addition for aroma. Hops can also be added during the fermentation or maturation phases, a process called dry hopping, typically targeting extraction of essential oils from the hops which lend strong aromatic profiles. Hops can also be added in the whirlpool, the end of the boiling phase in which the wort is stirred to create a vortex collecting all of the insoluble hop and grain residue at the bottom, enhancing the clarity of the wort. Some brewers whirlpool in the boil kettle itself, while others have a separate vessel. The wort is then passed through a heat exchanger to quickly cool the liquid as it is transferred to the fermenter. After a slight oxygenation step, the yeast is pitched and allowed to convert the sugars to alcohol and carbon dioxide. Typically for ales, *Saccharomyces cerevisiae* is pitched and incubated at 15 to 23° C. enhancing the ester and phenolic compound production of yeast, where lagers are pitched with *Saccharomyces pastorianus* and incubated at 10° C. or lower to reduce the yeast's flavor contribution. After primary fermentation, the beer can be transferred to a secondary fermentation, removing it from the spent yeast and allowing it to further condition and mature. Lagers typically can be stored for three to four weeks in cold storage to allow the remaining active yeast to consume the off flavor diacetyl. The conditioning can be used to add additional flavors (e.g., fruit, spice, or more hops). Some brewers will condition in bottles to also naturally carbonate the beer, while others can age in barrels or casks to further extract flavors and aromatics. After maturation, the beer can be filtered or pasteurized and transferred to the bright tank were it is carbonated, typically using forced carbonation with $CO_2$ tanks. The final beer product is then packaged in kegs, bottles, or cans.

In the context of the present disclosure, the process described herein is in certain embodiments for making wine. In some embodiments, the fermentable carbohydrates of the fermentable medium comprises glucose, fructose, sucrose, or combinations thereof. In one embodiment, the fermentable medium comprises glucose. In one embodiment, the fermentable medium comprises fructose. In one embodiment, the fermentable medium comprises sucrose. In one embodiment, the fermentable medium comprises glucose and fructose. In one embodiment, the fermentable medium comprises fructose and sucrose. In one embodiment, the fermentable medium comprises glucose, fructose, and sucrose. In some embodiments, the fermentable medium comprises about 2%, 4%, 6%, 8%, 10%, 12%, 14%, 16%, 18%, 20%, or 25% glucose. In one embodiment, the fermentable medium comprises about 10% glucose. In some embodiments, the fermentable medium comprises about 2%, 4%, 6%, 8%, 10%, 12%, 14%, 16%, 18%, 20%, or 25% sucrose. In one embodiment, the fermentable medium comprises about 8% sucrose. In some embodiments, the fermentable medium comprises about 0.5%, 1.0%, 1.5%, 2%, 2.5%, 3%, 3.5%, 5%, or 10% fructose. In one embodiment, the fermentable medium comprises about 2% sucrose.

In the wine-making process, after the harvest, the grapes are taken into a winery and prepared for primary ferment. Red wine is usually made from the must (pulp) of red or black grapes and fermentation occurs together with the grape skins. White wine is usually made by fermenting juice which is made by pressing crushed grapes to extract a juice; the skins are usually removed and play no further role. Rosé wines are either made from red grapes where the juice is allowed to stay in contact with the dark skins long enough to pick up a pinkish color (maceration or soignée), or (less commonly) by blending red wine with white wine. White and rosé wines extract little of the tannins contained in the skins. To start the primary fermentation yeast (e.g., the recombinant yeast host cell of the present disclosure, optionally in combination with endogenous or non-genetically modified yeasts) are added to the must or grape juice. The next step in the process in the making of red wine is referred to as the "malo-lactic conversion". This is a bacterial process which converts malic acid to lactic acid. In some embodiments, red wine can be transferred to oak barrels to mature for a period of weeks or months. In some embodiments, the process can include an additional, "secondary" fermentation inside the bottle (e.g., for sparkling wines such as champagnes).

In some embodiments, the fermentable medium comprises about 2%, 4%, 6%, 8%, 10%, 12%, 14%, 16%, 18%, 20%, or 25% higher-chained dextrins. In one embodiment, the fermentable medium comprises about 12% higher-chained dextrins.

The present disclosure also provides a fermented beverage obtainable or obtained by the processes described herein. Such beverage have a higher content of the hydrolyzed volatile flavor compound than a corresponding beverage which has been obtained from a yeast cell which does not include the heterologous nucleic acid molecule encoding the heterologous polypeptide having 1,4-β-glucosidase activity.

The present disclosure will be more readily understood by referring to the following examples, which are given to illustrate certain embodiments of the invention rather than to limit its scope.

EXAMPLE I—GROWTH OF YEAST STRAINS ON MALTOTRIOSE MEDIA

Different yeast strains utilize different sugar compounds for energy based on the availability of enzymes that break down complex sugars as well as energy optimization.

In biofuel yeast strains, the primary attributes required in the yeast strains are high alcohol tolerance (>15-20% w/v) and the ability to utilize and ferment, primarily monomeric sugars, in a rapid manner. The primary sugar in biofuel production, particularly corn ethanol, is glucose where starch is hydrolyzed into smaller dextrins via α-amylase and subsequently converted to glucose via glucoamylase. Because glucoamylase can efficiently hydrolyze maltotriose into glucose, many biofuel strains have lost the ability to utilize this trisaccharide. In particular, the loss of the AGT1 gene, which is a high affinity maltose/maltotriose transporter, is common among biofuel strains. Utilization of DP2/DP3 sugars requires a great deal of energy for yeast, accordingly yeast that have been domesticated for rapid growth and fermentation have found ways to conserve this energy, particularly in environments where low concentrations of complex sugars exist.

FIG. 1 shows the growth of a biofuel strain (M2390) compared to a wine strain (M11574) and a brewing strain (M14629) on maltotriose media. Most rapid and greatest growth is achieved by the brewing strain (M14629). The poor growth of the biofuel strain (M2390) indicates the inability or reduced capability to utilize maltotriose.

EXAMPLE II—ACTIVE EXPRESSION OF HETEROLOGOUS B-GLUCOSIDASE IN BREWING YEAST

Strain development. Experiments were conducted to determine the effects of expressing a 1,4-β-glucosidase enzyme in a brewing yeast. A total of five heterologous 1-4-β-glucosidases (see Table 1) were engineered into the following brewing yeast strains: M13175 (lager strain), M13176 (ale strain), and M14629 (ale strain). The ability of the resulting strains to degrade the p-nitrophenyl-β-D-glucopyranoside (pNPG) synthetic substrate was then evaluated as described below. Each of the five enzyme candidates were cloned into the corresponding strains via chromosomal integrations under control of the constitutive TEF2 promoter and IDP1 terminator. Table 2 provides for a summary of the strains used in the Examples.

TABLE 1

Heterologous 1,4-β-glucosidase enzymes.

| Enzyme Source | Genbank ID | SEQ ID NO |
|---|---|---|
| Aspergillus niger | CAB75696 | 1 |
| Aspergillus oryzae | XP_001816831 | 2 |
| Saccharomycopsis fibuligera | P22506 | 3 |
| Brettanomyces anonmalus | AKS48904 | 4 |
| Brettanomyces bruxellensis | AKS48905 | 5 |

TABLE 2

Description of strains evaluated for fermentation performance.

| Strain | Brewing strain type | Background | Heterologous β-glucosidase | Description |
|---|---|---|---|---|
| M13175 | lager strain | N.A. | N.A. | Wild type strain 1 |
| M14987 | lager strain | M13175 | SEQ ID NO: 1 | TEF2 promoter and IDP1 terminator |
| M14989 | lager strain | M13175 | SEQ ID NO: 2 | TEF2 promoter and IDP1 terminator |
| M13176 | ale strain | N.A. | N.A. | Wild type strain 2 |
| M17300 | ale strain | M13176 | SEQ ID NO: 1 | TEF2 promoter and IDP1 terminator |
| M17301 | ale strain | M13176 | SEQ ID NO: 2 | TEF2 promoter and IDP1 terminator |

TABLE 2-continued

Description of strains evaluated for fermentation performance.

| Strain | Brewing strain type | Background | Heterologous β-glucosidase | Description |
|---|---|---|---|---|
| M14629 | ale strain | N.A. | N.A. | Wild type strain 3 |
| M17298 | ale strain | M14629 | SEQ ID NO: 1 | TEF2 promoter and IDP1 terminator |
| M17299 | ale strain | M14629 | SEQ ID NO: 2 | TEF2 promoter and IDP1 terminator |

β-glucosidases assay. Transformants were grown in 96-well plates in 600 μl YP-DME (10 g/L yeast extract, 20 g/L peptone, 40 g/l dry malt extract) for 72 h at room temperature, centrifuged at 3 000 rpm for 5 min and the supernatant used in a microtiter β-glucosidase assay. The β-glucosidase assay was performed using 20 mM pNPG in 0.05 M citrate buffer pH 5.0. A total of 50 μl supernatant was added to 50 μl of pNPG substrate and incubated at room temperature for 30 min with the reaction stopped with 150 μl of 2M sodium carbonate. The absorbance was subsequently read at a 405 nm wavelength.

Figure 2:
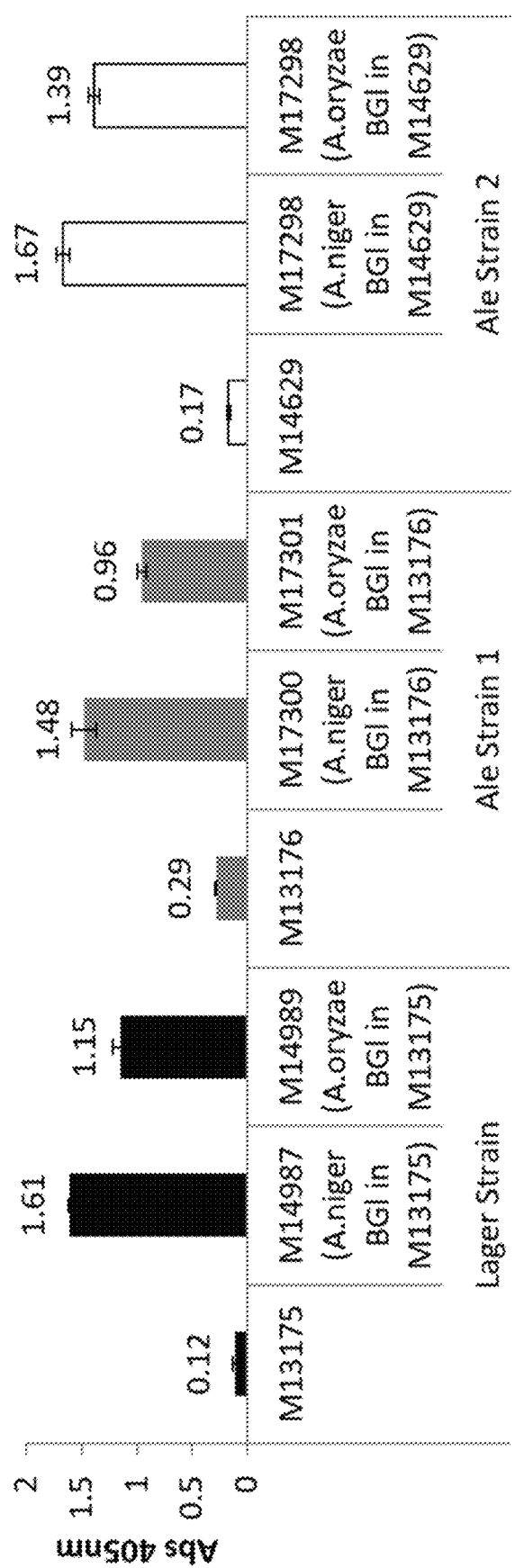
FIG. 2 shows the microtiter secreted β-glucosidases (BGI) enzyme assay on p-nitrophenyl-β-D-glucopyranoside (pNPG) synthetic substrate. Y axis is the absorbance read at a 405 nm wavelength. X axis is the strains evaluated, where M13175, M13176, and M14629 are wild-type control strains.

As seen in FIG. 2, both the *Aspergillus niger* and *Aspergillus oryzae* 1-4-β-glucosidases enzymes were active in all three backgrounds with the *Aspergillus niger* 1-4-β-glucosidases enzyme consistently being the most active. The *Saccharomycopsis fibuligera*, *Brettanomyces anonmalus* and *Brettanomyces bruxellensis* 1-4-β-glucosidases enzymes were not found to be active in the supernatant of recombinant yeast strains expressing them (data not shown).

Lab-scale wort fermentation. Transformants for each active secreted 1-4-β-glucosidase enzyme (*A. niger* or *A. oryzae* 1-4-β-glucosidases expressing transformants) were further screened in a lab-scale wort fermentation to evaluate effects on fermentation kinetics due to the heterologous secreted enzyme. Strains were grown overnight in 50 mL YP-DME at room temperature and the ale strains inoculated at 0.125 g dry cell weight (DCW) and the lager strains at 0.25 g DCW into 12.5° Plato dry malt extract and 0.01% isomerized hop oil. The fermentations were performed at 175 mL volumes in 250 mL conical tubes at either room temp (20° C.) for the ales or 10° C. for the lagers. The fermentations were performed in duplicate. Specific gravity was measured using a refractometer at 0, 48, 96, 144, and 192 h.

Figure 3:
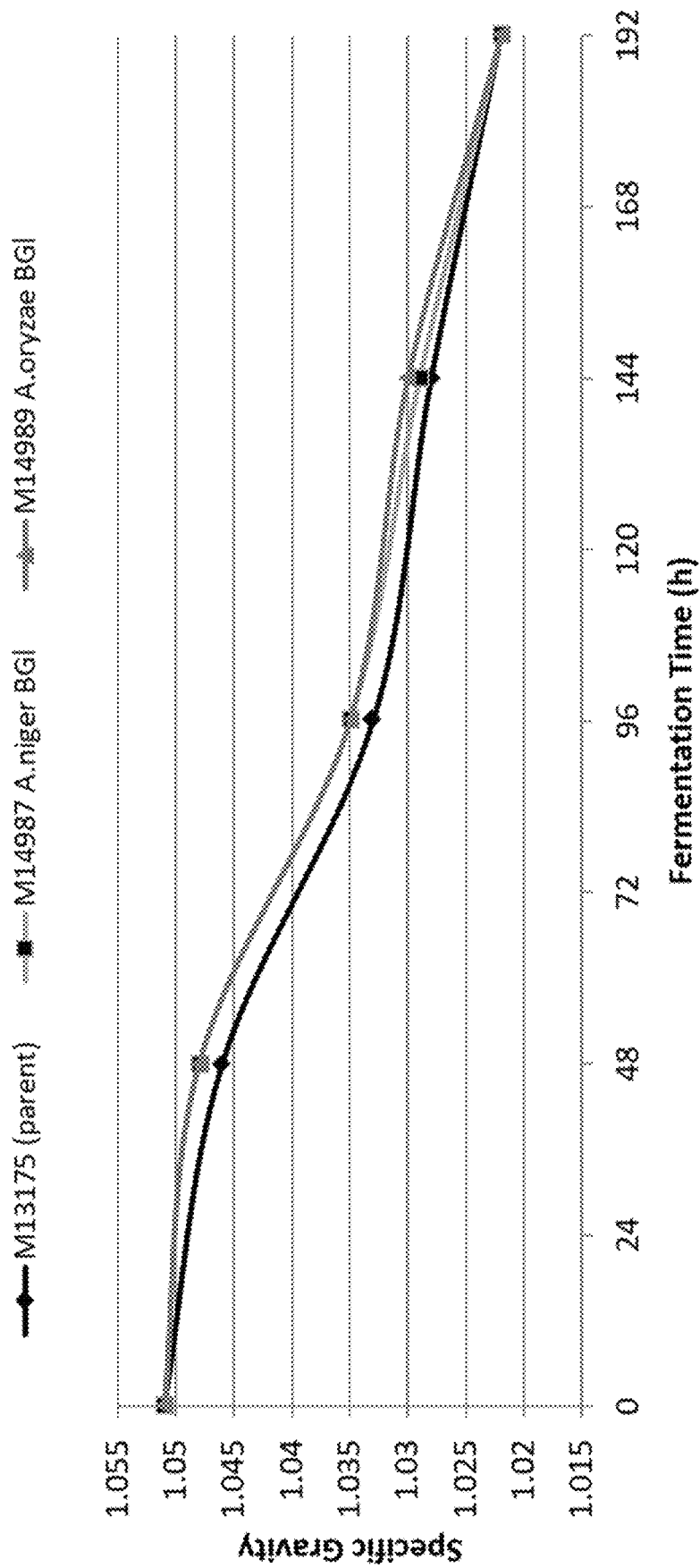
FIG. 3 shows the specific gravity profiles of wild-type M13175 strain and the corresponding engineered strains expressing the *Aspergillus niger* (M14987) or *Aspergillus oryzae* (M14989) 1-4-β-glucosidases enzyme in a lab-scale lager fermentation at 10° C., 12.5° plato dry malt extract, 0.01% hop oil. Y axis is the specific gravity. X axis is fermentation time in hours. Data points: diamond (‡) for strain M13175, square (□) for strain M14987, and triangle (Δ) for strain M14989.
Figure 4:
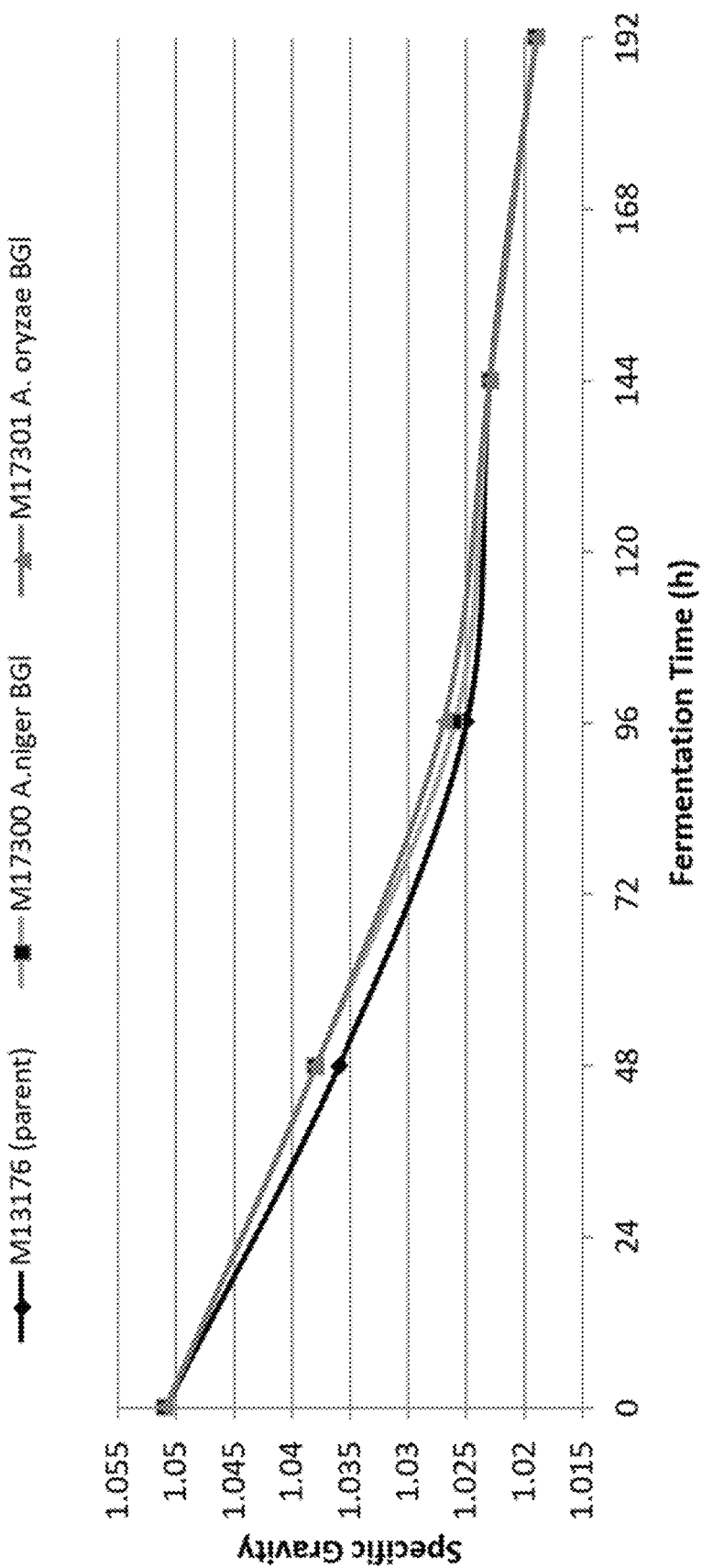
FIG. 4 shows the specific gravity profiles of wild-type M13176 strain and the corresponding engineered strains expressing the *Aspergillus niger* or *Aspergillus oryzae* 1-4-β-glucosidases enzyme in a lab-scale ale fermentation at 20° C., 12.5° plato dry malt extract, 0.01% hop oil. Y axis is the specific gravity. X axis is fermentation time in hours. Data points: diamond (‡) for strain M13176, square (□) for *Aspergillus niger* 1-4-β-glucosidases expressing strain M17300, and triangle (Δ) for *Aspergillus oryzae* 1-4-β-glucosidases expressing strain M17301.
Figure 5:
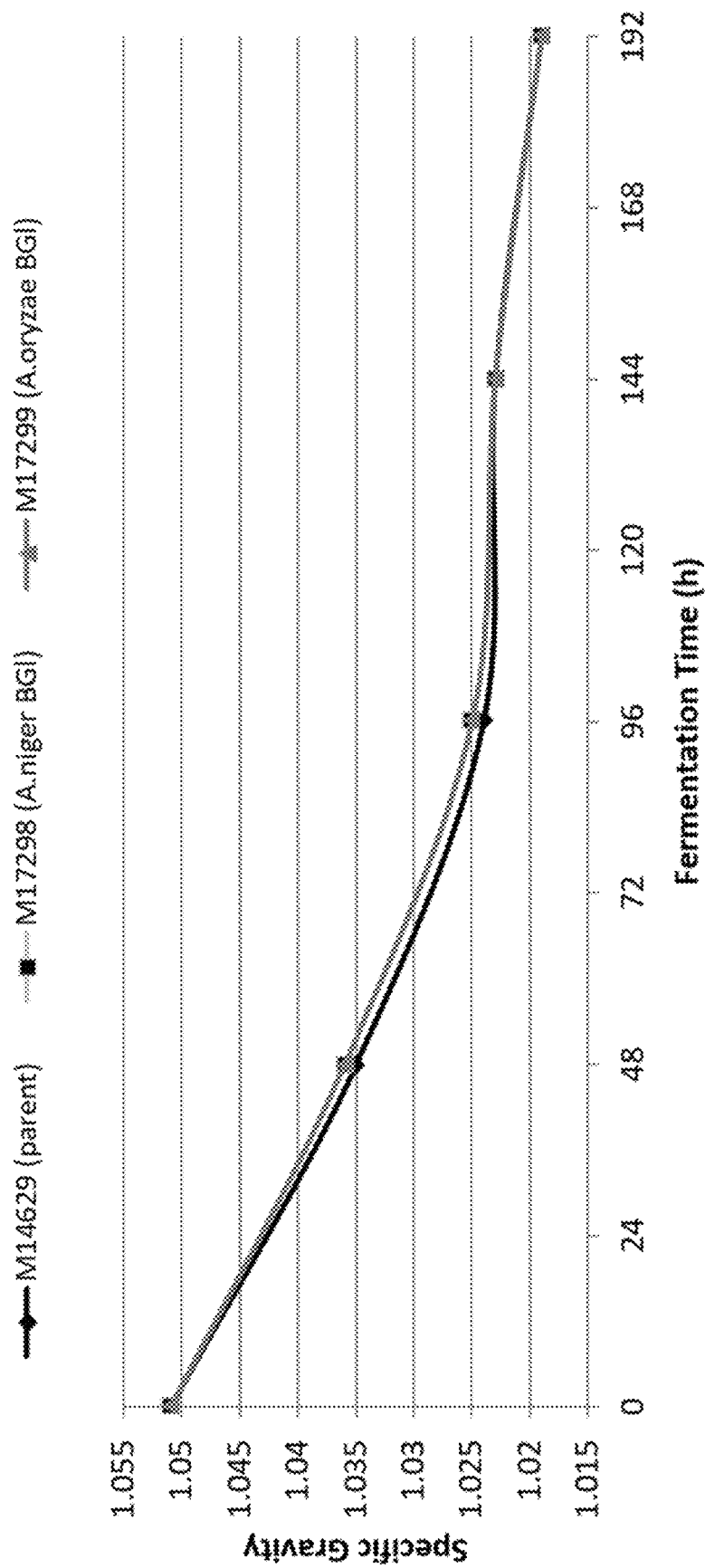
FIG. 5 shows the specific gravity profiles of wild-type M14629 strain and the corresponding engineered strains expressing the *Aspergillus niger* or *Aspergillus oryzae* 1-4-β-glucosidases enzyme in a lab-scale ale fermentation at 20° C., 12.5° plato dry malt extract, 0.01% hop oil. Y axis is the specific gravity. X axis is fermentation time in hours. Data points: diamond (‡) for strain M14629, square (□) for *Aspergillus niger* 1-4-β-glucosidases expressing strain M17298, and triangle (Δ) for *Aspergillus oryzae* 1-4-β-glucosidases expressing strain M17299.

For all lager and ale 1-4-β-glucosidases transformants, there was only a slight decrease in fermentation kinetics with all strains finishing with their respective parents between 144 h and 192 h (FIGS. 3 to 5).

EXAMPLE III—INCREASING AROMATIC COMPOUNDS IN BEER USING STRAINS EXPRESSING HETEROLOGOUS B-GLUCOSIDASE

Figure 6:
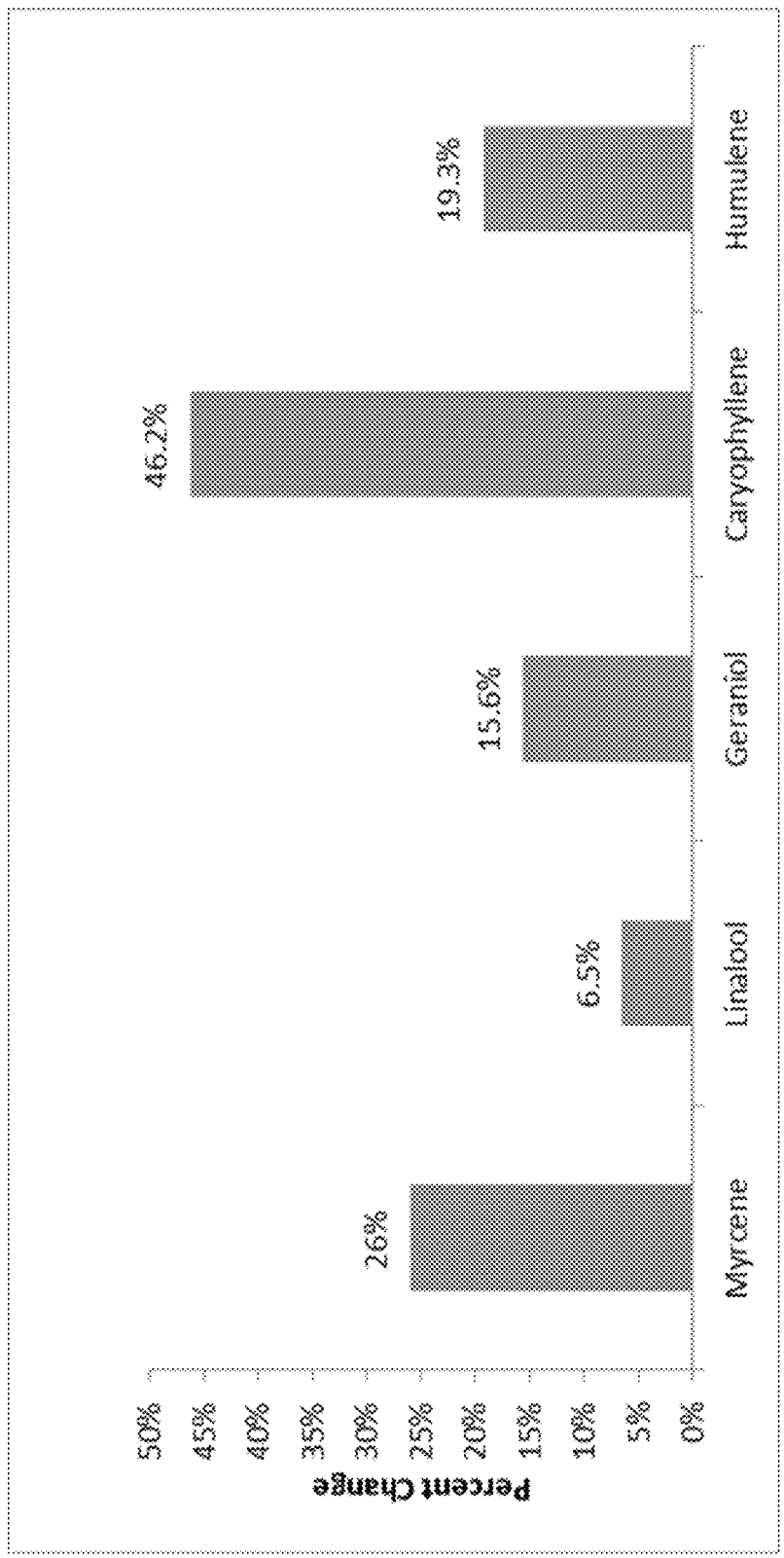
FIG. 6 shows gas chromatography head space analysis of a dry-hopped American Indian Pale Ale (IPA) fermented using engineered *Aspergillus niger* 1-4-β-glucosidase enzyme expressing M17298 strain compared to that fermented using wild-type strain M14629. Y axis is the percentage increase. X axis is the essential oils analyzed by the head space analysis. The percentage increase for each essential oil is indicated above the each bar.

Lab-scale fermentation. The engineered strain, M17298 expressing the *Aspergillus niger* 1-4-β-glucosidase enzyme (described in Example I), was subsequently evaluated in a lab-scale fermentation (2.5 gallons) versus the parental control (M14629) using an American India Pale Ale (IPA) recipe in which Centennial hops were added during the boil (60 min, 20 min, 5 min) and 1 oz of Centennial added to the secondary as a dry hop. After 7 days of dry hopping, samples were collected and submitted for gas chromatography/mass spectrometry (GC/MS) analysis. Beer samples were analyzed by headspace-gas chromatography coupled to a mass spectrometer (HS-GC/MS). Samples (5 mL) were mixed with 1 g NaCl in a headspace vial and incubated at 70° C. for 5 min. The headspace was then sampled (1 mL) and injected onto the GC/MS. Compounds were separated on a StabilWax® MS30 column ramped from 35° C. to 200° C. at a rate of 5° C/min. The helium flow rate was 1 mL/min and the injector was held at 120° C. Compounds were identified based on retention times and comparison of mass spectra to the NIST database. Peak areas were measured for specific essential oils, allowing comparison between samples to determine the percent increase with the M17298 1-4-β-glucosidase expressing strain, as shown in FIG. 6 and Table 3.

TABLE 3

Percentage increase in essential oils in fermentation product using M17298 *Aspergillus niger* 1-4-β-glucosidase enzyme expressing strain compared to parent control (M14629).

| Essential Oil | Percentage Increase |
|---|---|
| Myrcene | 26% |
| Linalool | 6.5% |
| Geraniol | 15.6% |
| Caryophyllene | 46.2% |
| Humulene | 19.3% |

Figure 7:
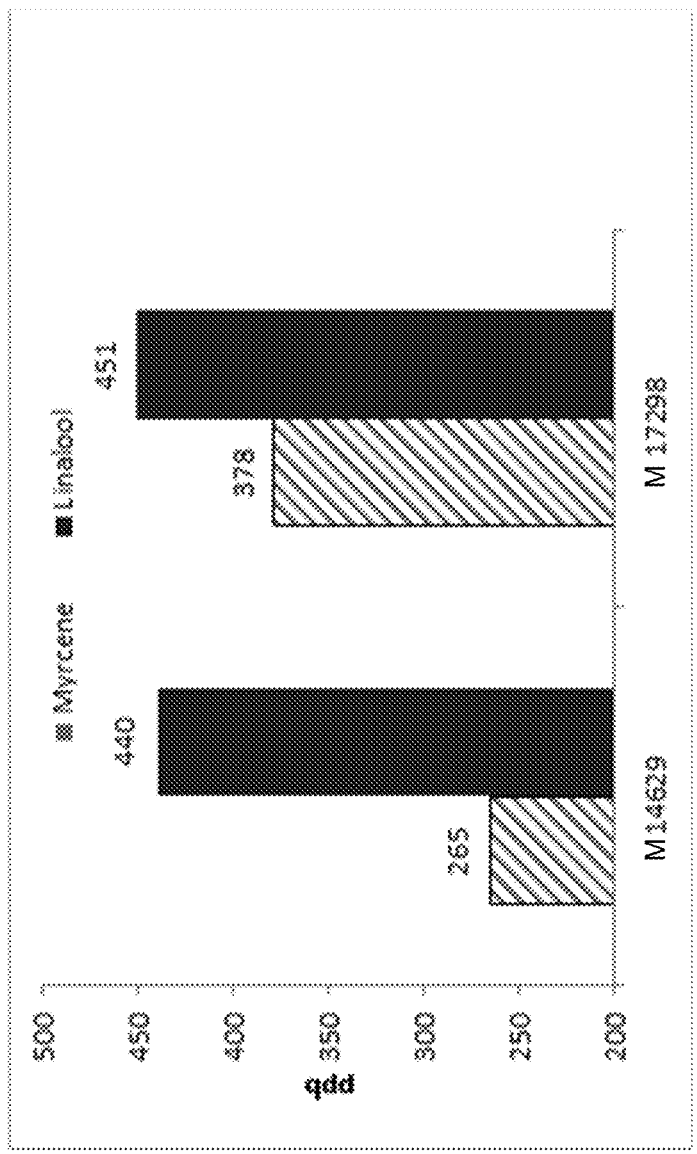
FIG. 7 shows the gas chromatography quantification of a liquid methyl-tert-butyl ether MTBE extracted American IPA fermentation using engineered *Aspergillus niger* 1-4-β-glucosidase enzyme expressing M17298 strain compared to that fermented using wild-type strain M14629. Y axis is ppb. X axis shows the results obtained for each of the strains M14629 and M17298. Solid black bars represents myrcene, striped bars represents linalool.

A methyl-tert-butyl ether (MTBE) liquid extraction was also performed to evaluate potential quantification of myrcene and linalool. As seen FIG. 7, the beer made using M17298 β-glucosidases expressing strain had 451 ppb and 378 ppb linalool and myrcene, which is 2.5% and 42.6% more than the control beer obtained with M14629, respectively.

A variety of aromatic and flavor compounds were also measured using mass spectroscopy as described above and provided a normalized response time to show the difference between the two fermentations. The beer made using M17298 β-glucosidases expressing strain had measureable differences in various aromatic and flavor compounds.

Figure 8:
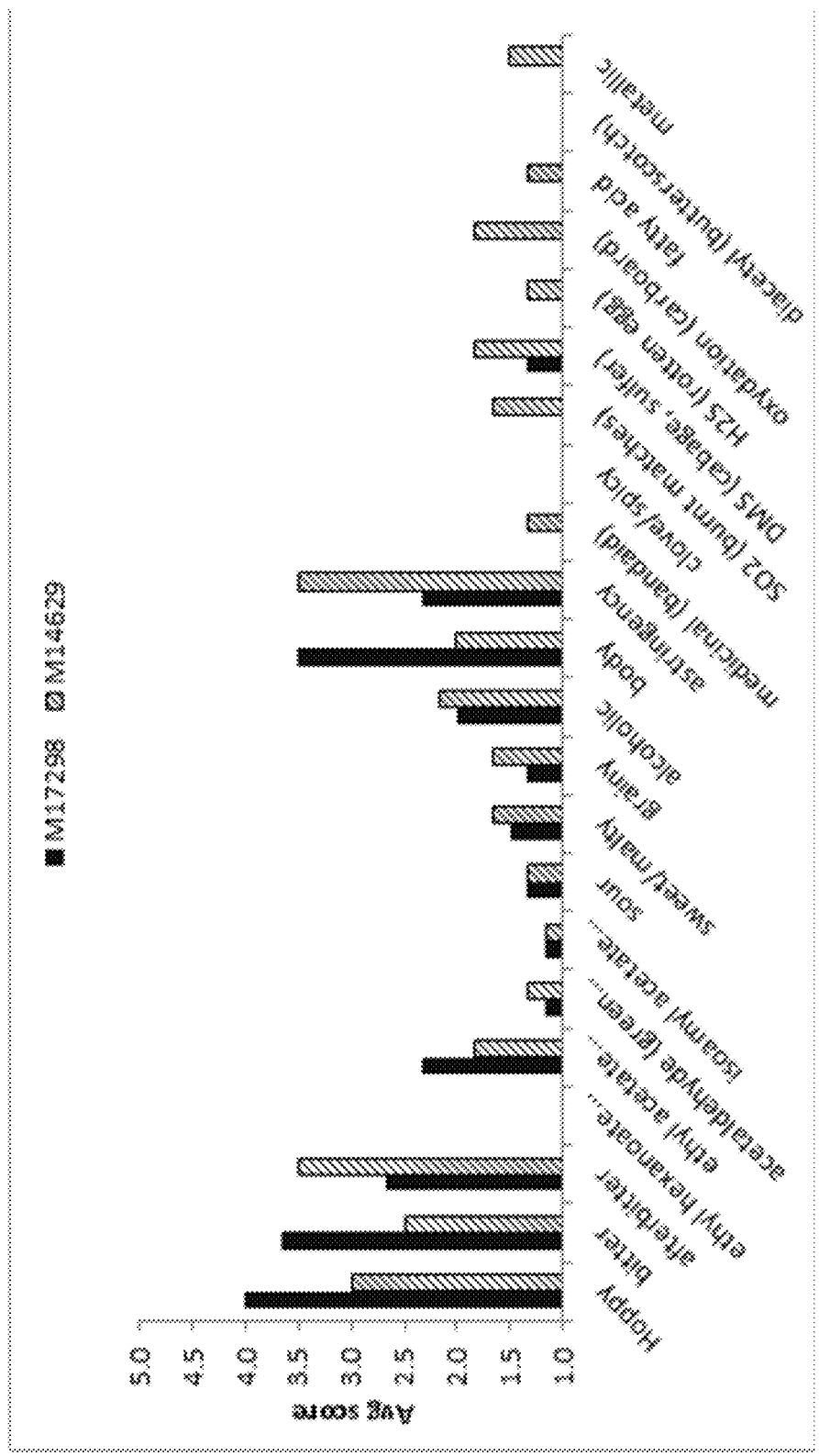
FIG. 8 shows the scoring of tasting notes comparing beers fermented with either the β-glucosidase engineered strain M17298 (black bar), or the control parent strain M14629 (striped bar). Each tasting characteristic was rated 1-5 (lowest to highest) and averaged between the 6 tasters. Y axis is average score. X axis is the taste notes.

A blind tasting was conducted with a 6 person panel using the above American IPA recipe in which Centennial hops were added during the boil (60 min, 20 min, 5 min) and 1 oz of Centennial added to the secondary as a dry hop for 7 days. The 5 gallon wort was split into 2.5 gallons and fermented with either the engineered strain, M17298 expressing the *A. niger* BGI, or the parental strain, M14629. In summary, 5 out of the 6 people overwhelmingly preferred the beer fermented with the β-glucosidase expressing yeast, strain M17298. The panel was also provided a scoring sheet rating key tasting notes from 1 (lowest) to 5 (highest). On average, the tasters noted an increased hoppiness and bitterness with a reduced astringency and afterbitter profile in the M17298 beer. Also of significance was a dramatic increase in overall body and mouthfeel for the M17298 beer (see FIG. 8).

What is claimed is:

1. A recombinant yeast host cell for improving a flavor profile of a fermented beverage by hydrolyzing a non-volatile conjugate, wherein the fermented beverage is obtained by fermentation of a fermentable medium with the recombinant yeast host cell, and the non-volatile conjugate is of formula (I):

VFC—SM     (I)

where: VFC is a flavor compound that is volatile when released from the non-volatile conjugate, SM is a sugar molecule, and "—" is a β-glycosidic linkage covalently attaching the VFC to the SM, and capable of being hydrolyzed;

wherein the recombinant yeast host cell:

has a heterologous nucleic acid molecule encoding one or more heterologous polypeptide having 1,4-β-glucosidase activity for hydrolyzing the β-glycosidic linkage to release the VFC from the non-volatile conjugate;
has a native ethanol production pathway; and
is a brewing or wine strain.

2. The recombinant yeast host cell of claim 1, wherein the heterologous polypeptide is a secreted polypeptide and/or a cell-associated polypeptide.

3. The recombinant yeast host cell of claim 1, wherein the VFC is a terpenoid.

4. The recombinant yeast hot cell of claim 1, wherein the heterologous polypeptide having 1,4-β-glucosidase activity:
   a) has the amino acid sequence corresponding to positions 20 to 860 of SEQ ID NO: 1,
   b) has the amino acid sequence of SEQ ID NO: 2,
   c) corresponds to positions 18 to 876 of SEQ ID NO: 3,
   d) has the amino acid sequence corresponding to positions 18-841 of SEQ ID NO: 4,
   e) has the amino acid sequence of SEQ ID NO: 5,
   f) is a variant of any one of a) to e) having 1,4-β-glucosidase activity, or
   g) is a fragment thereof of any one of a) to f) having 1,4-β-glucosidase activity.

5. The recombinant yeast host cell of claim 1 expressing a maltotriose transporter.

6. The recombinant yeast host cell of claim 1 being from the genus *Saccharomyces* sp.

7. The recombinant yeast host cell of claim 6 being from the species *Saccharomyces cerevisiae* or from the species *Saccharomyces pastorianus*.

8. A composition comprising the recombinant yeast host cell of claim 1 and an emulsifier.

9. A process for making a fermented beverage from a fermentable medium comprising fermentable carbohydrates and a non-volatile conjugate of formula (I):

VFC—SM  (I)

where: VFC is a flavor compound that is volatile when released from the non-volatile conjugate,
SM is a sugar molecule, and
"—" is a β-glycosidic linkage covalently attaching the VFC to the SM, and capable of being hydrolyzed;

the process comprising contacting the recombinant yeast host cell of claim 1 with the fermentable medium under conditions to allow the hydrolysis of the β-glycosidic linkages during and/or after the conversion of at least some of the fermentable carbohydrates into ethanol by the recombinant yeast host cell; wherein:
   the fermentable medium comprises the non-volatile conjugate prior to the addition of the recombinant yeast host cell or composition; and/or
   the fermentable medium is supplemented with the non-volatile conjugate at the same time or after the addition of the recombinant yeast host cell or composition.

10. The process of claim 9, wherein the contacting step occurs, at least in part, at a temperature between about 3 and about 28° C.

11. The process of claim 10, further comprising supplementing the fermentable medium with a hop before, during, and/or after the contacting step.

12. The process of claim 11, wherein the fermented beverage is beer.

13. The process of claim 12, wherein the beer is ale.

14. The process of claim 13, wherein the contacting step occurs, at least in part, at a temperature between about 15 and about 24° C.

15. The process of claim 12, wherein the beer is lager.

16. The process of claim 15, wherein the contacting step occurs, at least in part, at a temperature between about 3 and about 15° C.

17. The process of claim 12, wherein the fermentable medium comprises a majority of maltose and/or maltotriose.

18. The process of claim 9, wherein the fermented beverage is wine.

19. The process of claim 18, wherein the contacting step occurs, at least in part, at a temperature between about 12 and about 28° C.

20. The process of claim 18, wherein the fermentable medium comprises glucose, fructose, sucrose, or combinations thereof.

* * * * *